(12) United States Patent
Liau

(10) Patent No.: US 7,192,704 B2
(45) Date of Patent: Mar. 20, 2007

(54) METHODS FOR DETECTION AND TREATMENT OF NEURAL CANCERS

(75) Inventor: Linda M. Liau, Los Angeles, CA (US)

(73) Assignee: The Regents of the University of California, Oakland, CA (US)

( * ) Notice: Subject to any disclaimer, the term of this patent is extended or adjusted under 35 U.S.C. 154(b) by 678 days.

(21) Appl. No.: 10/382,945

(22) Filed: Mar. 6, 2003

(65) Prior Publication Data

US 2003/0170247 A1    Sep. 11, 2003

Related U.S. Application Data

(62) Division of application No. 09/795,714, filed on Feb. 28, 2001, now Pat. No. 6,558,668.

(60) Provisional application No. 60/185,321, filed on Feb. 28, 2000.

(51) Int. Cl.
C12Q 1/68 (2006.01)
G01N 33/53 (2006.01)

(52) U.S. Cl. .......................... 435/6; 436/501; 436/518; 435/7.1; 435/7.23

(58) Field of Classification Search ............... None
See application file for complete search history.

(56) References Cited

U.S. PATENT DOCUMENTS 5,416,192 A    5/1995    Shoyab et al.
5,476,839 A    12/1995   Scott et al.

OTHER PUBLICATIONS

Liau, L.M. et al., "Identification of a human glioma-associated growth factor gene, granulin, using differential immune-absorption", Cancer Research, American Association for cancer research, Baltimore, MD, US, vol. 60, Mar. 1, 2000, pp. 1353-1360. XP002963369.
Bateman, Andrew et al., "Granulins, A Novel Class of Peptide From Leukocytes", Biochemical and Biophysical Research Communications, vol. 173, No. 3. Dec. 31, 1990, pp. 1161-1168.
Bhandari, Vijay et al., "The Complementary Deoxyribonucleic Acid Sequence, Tissue Distribution, and Cellular Localization of the Rat Granulin Precursor", Endocrinolgy, vol. 133, No. 6, 1993, pp. 2682-2689.
Culouscou, Jean-Michel et al., "Biochemical Analysis of the Epithelin Receptor," The Journal of Biological Chemistry, vol. 268, No. 14, May 15, 1993, pp. 10458-10462.
Dictxmann, Kout et al., "Coexpression of epidermal growth factor receptor protein and c-erbB-2 oncoprotein in human astrocytic tumors. An immunohistochemical study." Zentralblatt fur Pathologie, vol. 140, 1994, pp. 335-341.
Liau, Linda, "Identification and characterization of tumor-associated genes in malignant glioonas", Dissertation Abstracts International, vol. 60, No. 12, Jun. 2000, p. 5958-B.
Liau, Linda, "Identification of a Putative Glioma-Sepcific EGF-Like Growth Factor Using Differential Immuno-Absorption Coupled to cDNA Microarray Hybridization", Abstracts from the Third Annual Meeting of the Society for Neuro-Oncology Nov. 12-15, 1998, Neuro-Oncology, Jan. 1999, p. 536.
Liang, Peng et al., "Differential Display and Cloning of Messenger RNAs from Human Breast Cancer versus Mammary Epithelial Cells", Cancer Research, vol. 52, Dec. 15, 1992, pp. 6966-6968.
Lu, Runqing et al., "Stimulation of PC Cell-Derived Growth Factor (Epithelin/Granulin Precursor) Expression by Estradiol in Human Breast Cancer Cells", Biochemical and Biophysical Research Communications, vol. 256, 1999, pp. 204-207.
Lucas, Sophie et al., "Identification of a New MAGE Gene with Tumor-Specific Expression by Representational Difference Analysis", Cancer Research, vol. 58, Feb. 15, 1998, pp. 743-752.
Nagane, Motoo et al., "Advances in the molecular genetics of gliomas," Current Opinion in Oncology, vol. 9, 1997, pp. 215-222.
Schena, Mack et al., "Quantitative Monitoring of Gene Expression Patterns with a Complementary DNA Microarray", Science, vol. 270, Oct. 20, 1995, pp. 467-470.
Uchiyama, Christopher M. et al., "Differential Display of Messenger Ribonucleic Acid: A Useful Technique for Analyzing Differential Gene Expression in Human Brain Tumors," Neurosurgery, vol. 37, No. 3, Sep. 1995, pp. 464-470.
von Bossanyi, Peter et al., "Correlation of TGF-alpha and EGF-Receptor Expression with Proliferative Activity in Human Astrocytic Gliomas," Pathology Research and Practice, vol. 194, 1998, pp. 141-147.
Welford, Scott M. et al., "Detection of differentially expressed genes in primary tumor tissues using representational differences analysis coupled to microarray hybridization", Nucleic Acids Research, vol. 26, No. 12, 1998, pp. 3059-3065.
Zanocco-Marani, Tommaso et al., "Biological Activities and Signaling Pathways of the Granulin/Epithelin Precursor", Cancer Research, vol. 59, Oct. 15, 1999, pp. 5331-5340.

(Continued)

Primary Examiner—Misook Yu
(74) Attorney, Agent, or Firm—Canady + Lortz LLP; Karen S. Canady

(57) ABSTRACT

The invention provides a method for inhibiting proliferation of neural cells. The neural cells can be tumor cells, glial cells, neuronal cells, and cells of the central or peripheral nervous systems. The method comprises contacting a neural cell with a molecule that disrupts the biological activity of a granulin molecule. In one embodiment, the molecule is an antibody directed against a granulin peptide. In other embodiments, the molecule is an antisense nucleotide directed against a granulin nucleic acid molecule, or a vaccine comprising a granulin peptide or a polynucleotide encoding a granulin peptide. The invention additionally provides methods for detecting and treating cancer in a neural tissue using granulin-related molecules. Also provided is a method for indenting differentially expressed gene products that are translated from mRNA species, using antibody-based screening of a cDNA expression library. This method, termed differential immuno-absorption (DIA), can be coupled to cDNA microarray hybridization and used in the identification of genes that play a role in the malignant progression of cancer.

11 Claims, 8 Drawing Sheets

OTHER PUBLICATIONS

Zhang, Haith et al., "Inhibition of tumorigenicity of the teratoma PC cell line by transfection with antisense cDNA for PC cell-derived growth factor (PCDGF, epithelin/granulin precursor)", *Proc. Natl. Acad. Sci. USA,* vol. 95, Nov. 1998, pp. 14202-14207.

Zhou, Jinn et al., "Purification of an Autocrine Growth Factor Homologous with Mouse Epithelin Precursor from a Highly Tumorigenic Cell Line," *The Journal of Biological Chemistry,* vol. 268, No. 15, May 25, 1993, pp. 10863-10869.

He, et al, 1999, Cancer Research, 59:3222-3229.

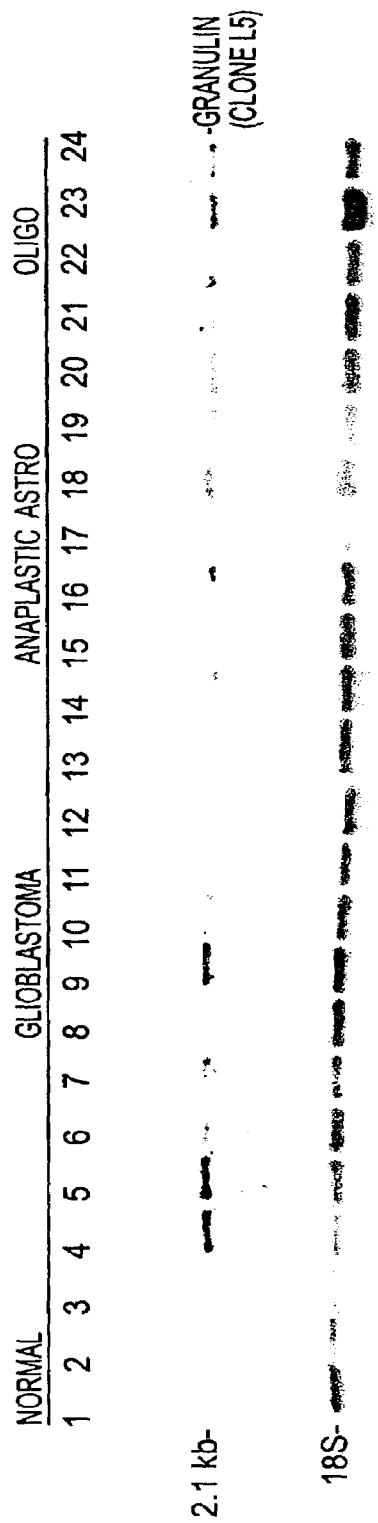
FIG. 3A
FIG. 3B

FIG. 4A
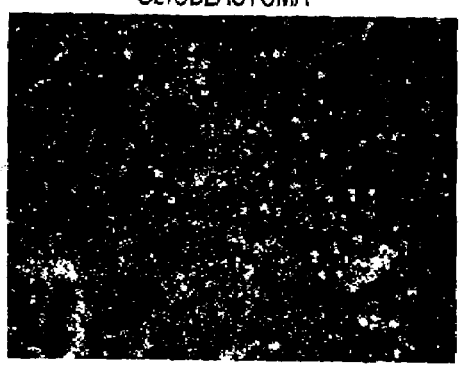
FIG. 4B
FIG. 4C
FIG. 4D

[GRANULIN D PEPTIDE]
0 ng/ml

[GRANULIN D PEPTIDE]
500 ng/ml

METHODS FOR DETECTION AND TREATMENT OF NEURAL CANCERS

This application is a divisional of U.S. patent application Ser. No. 09/795,714, filed Feb. 28, 2001, now U.S. Pat. No. 6,558,668, issued May 6, 2003, which claims benefit of U.S. provisional application 60/185,321, filed Feb. 28, 2000, the entire contents of which are incorporated herein by reference. Throughout this application various publications are referenced. The disclosures of these publications in their entireties are hereby incorporated by reference into this application in order to describe more fully the state of the art to which this invention pertains. Some of these references are indicated by numbers in parentheses. Citations corresponding to these reference numbers can be found at the end of the specification.

TECHNICAL FIELD OF THE INVENTION

The present invention relates generally to detection and therapy of cancer of the nervous system. The invention is more specifically related to granulin and granulin-related molecules as therapeutic and diagnostic targets. Granulin antibodies and antisense nucleotides can be used in vaccines and pharmaceutical compositions for the treatment of cancers of the central nervous system, as well as in methods of detecting and assessing the malignancy of such cancers. The invention further provides methods for identifying molecules useful in the treatment and detection of neural cancers.

BACKGROUND OF THE INVENTION

Cancer and infectious disease are significant health problems throughout the world. Although advances have been made in detection and therapy of these diseases, no vaccine or other universally successful method for prevention or treatment is currently available. Current therapies, which are generally based on a combination of chemotherapy or surgery and radiation, continue to prove inadequate in many patients.

Cancer is the result of cumulative multiple genetic mutations, which result in the activation of oncogenes and/or the inactivation of tumor suppressor genes. It is the differential expression of these critical genes and their downstream effectors that enables cells to override growth controls and undergo carcinogenesis (1, 2). The pathological changes that arise in cancer, whether caused by a single gene mutation or multiple genetic alterations, are essentially driven by changes in gene expression (1, 2). In the malignant progression of astrocytic cancers, it has been shown that accumulation of multiple genetic lesions underlies the neoplastic process. These lesions include mutations of the genes p53, p16, RB, and PTEN, as well as amplification of CDK4 and EGFR (3, 4). Although these known genetic abnormalities have been well-documented in the formation of the most malignant brain tumor, glioblastoma, recent insight into the extent of gene expression differences underlying malignancy reveals that hundreds of gene transcripts may be expressed at significantly different levels between normal and neoplastic cells (5). Therefore, there is considerable room for the identification of novel genes that are differentially expressed in brain tumor cells to further our understanding of the complex molecular basis of these neurological cancers. Furthermore, this endeavor has direct clinical relevance if combined with the development of innovative rational therapies that specifically target these differentially expressed gene products.

A variety of methods are currently employed to isolate genes associated with particular differential phenotypes. Subtractive hybridization (6), differential display (DD) (7–10), representational difference analysis (RDA) (11–14), serial analysis of gene expression (SAGE) (5, 15), and suppression subtractive hybridization (SSH) (16, 17) all allow for the cloning and identification of differentially expressed sequences. While all these techniques identify tissue-enriched mRNAs, none select for tissue-specific proteins. There remains a need for a differential screening technique that provides actual confirmation of the presence of a protein product, not just the capacity to synthesize a protein. In addition, there is a need for proteins with antigenic determinants that may be recognized by the immune system.

SUMMARY OF THE INVENTION

The invention meets these needs by providing methods for the treatment and detection of cancers of the nervous system. In one embodiment, the invention provides a method for inhibiting proliferation of neural cells. The neural cells can be tumor cells, glial cells, neuronal cells, and cells of the central or peripheral nervous systems. Examples of tumor cells include, but are not limited to, glioblastoma, astrocytoma, oligodendroglioma, ependymoma, choroid plexus papilloma, medulloblastoma, Schwannoma, neurofibroma, neurilemmoma cells, as well as neuronal, meningial, pineal or pituitary tumor cells. The method:comprises contacting a neural cell with a molecule that disrupts the biological activity of a granulin molecule. In one embodiment, the molecule is an antibody directed against a granulin peptide. In other embodiments, the molecule is an antisense nucleotide directed against a granulin nucleic acid molecule, or a vaccine comprising a granulin peptide or a polynucleotide encoding a granulin peptide. The invention further provides a method for treating cancer of the nervous system in a subject comprising administering to the subject a molecule that disrupts the biological activity of a granulin molecule.

The invention additionally provides a method for detecting cancer in a neural tissue comprising contacting the tissue with a molecule that recognizes and binds a granulin molecule. The molecule can be, for example, an antibody directed against a granulin peptide, or an antisense nucleotide directed against a granulin nucleic acid molecule.

The invention provides a method for identifying a molecule that inhibits proliferation of neural cancer cells. The method comprises contacting a candidate molecule with a granulin molecule and determining whether the candidate molecule disrupts the biological activity of the granulin molecule. Disruption of the biological activity of the granulin molecule is indicative of a molecule that inhibits proliferation of neural cancer cells.

The invention provides a method for identifying differentially expressed gene products that are translated from mRNA species, using antibody-based screening of a cDNA expression library. This method, termed differential immuno-absorption (DIA), can be coupled to cDNA microarray hybridization and used in the identification of genes that play a role in the malignant progression of cancer. The method for identifying proteins differentially expressed in a target tissue comprises linking a target tissue homogenate to a first substrate, and passing an antiserum raised against the target tissue homogenate over the first substrate to elute antibodies that bind the target tissue. The method further comprises linking a control tissue homogenate to a second substrate, and passing the eluted antibodies over the second substrate to obtain target antibodies that bind proteins present in the target tissue and not proteins present in the control tissue. The target antibodies so obtained are then used to screen a nucleic acid expression library containing proteins expressed in the target tissue. Proteins bound by the target antibodies are identified as differentially expressed in the target tissue.

The invention thereby provides novel proteins, antibodies and nucleotides identified by this method.

In addition, the invention provides a method of identifying a protein that is differentially expressed in a neural cancer comprising screening a first library of cells associated with neural cancer and a second library of non-tumor neural cells with a nucleic acid molecule encoding a candidate protein. Increased hybridization of the nucleic acid molecule with the first library relative to the second library is indicative of a protein that is differentially expressed in neural cancer. In one embodiment, the screening comprises a cDNA microarray assay.

BRIEF DESCRIPTION OF THE FIGURES

FIGS. 3A–B shows granulin expression in human tissues. (A) Northern blot analysis of granulin mRNA in normal and tumorigenic brain tissues. Lanes 1–3 were non-tumorigenic brain tissues taken from a surgical resection for epilepsy (lane 1), surgical decompression for trauma (lane 2), and autopsy normal brain (lane 3). Lanes 4–24 were surgically resected brain tumor tissues that were pathologically confirmed to be glioblastomas (WHO grade IV, lanes 4–15), anaplastic astrocytomas (WHO grade III, lanes 16–21), low-grade oligodendrogliomas (WHO grade II, lane 22), or anaplastic oligodendrogliomas (WHO grade III, lanes 23–24). All surgical specimens were immediately snap frozen in the liquid nitrogen in the operating room. The blot was exposed for 48 hours with intensifying screen. (B) Northern blot analysis of granulin mRNA in various human peripheral organs. Tissue specimens were taken at autopsy from normal brain (lane 1), lung (lane 2), heart (lane 3), skeletal muscle (lane 4), pancreas (lane 5), liver (lane 6), testes (lane 7), spleen (lane 8), kidney (lane 9), and adrenal gland (lane 10). This blot was exposed for 2 weeks with intensifying screens. As a loading control, the same blots were reprobed with 18S cDNA and exposed for 1 hour without a screen.

FIGS. 4A–D shows granulin mRNA in situ hybridization in normal and tumorigenic brain tissues. (Top) Dark-field photomicrographs of representative sections through normal white matter (A) and glioblastoma tissues (B) processed for in situ hybridization using [$^{35}$S]-labeled granulin cRNA. Note the significantly greater hybridization densities (white silver grains) in the glioblastoma compared with the normal brain section. Original magnification=40×. (Bottom) High-powered bright-field image of in situ hybridization of [$^{35}$S]-labeled granulin cRNA in sections of normal brain (C) and tumor (D) counterstained with hematoxylin and eosin. Note that the density and distribution of the intensely hybridizing areas (arrows) appear to be within tumor cells and not in the surrounding tissue. Also note the relative lack of labeling in the non-tumor glial cells. Original magnification=200×.

DETAILED DESCRIPTION OF THE INVENTION

Figure 1:
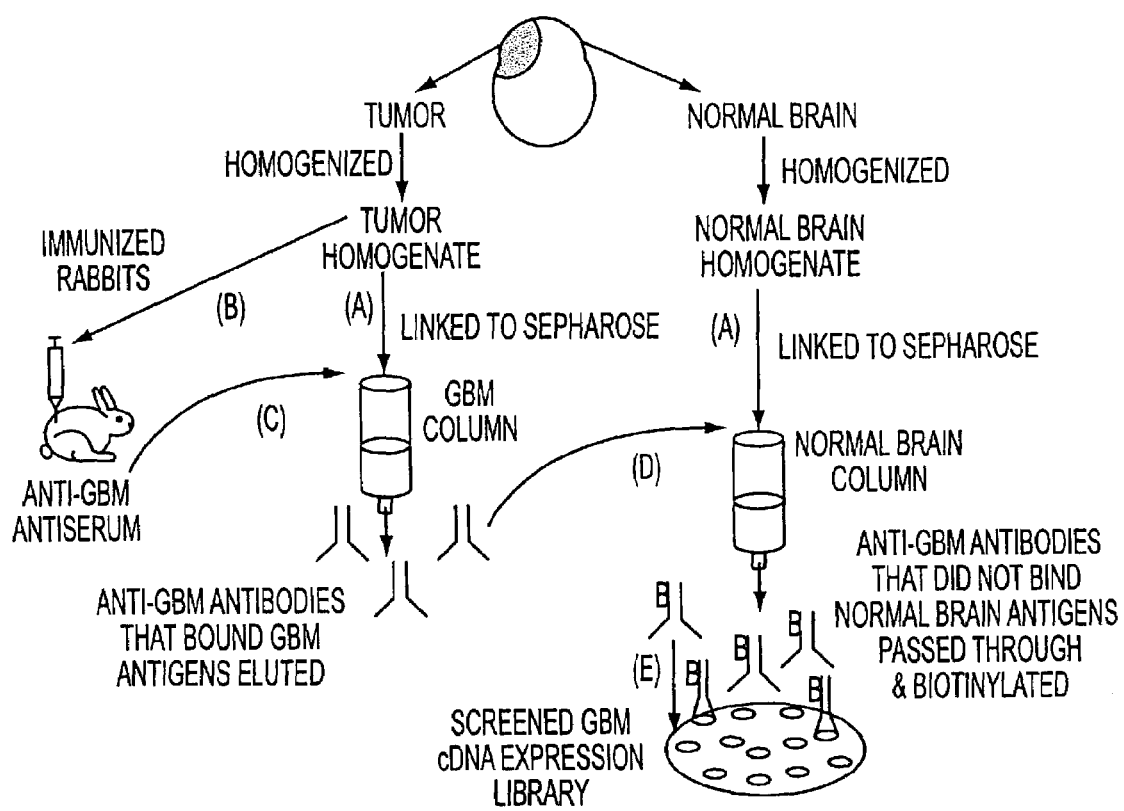
FIG. 1 is a schematic diagram of strategy for differential immuno-absorption (DIA). Glioblastoma (GBM) tumor and normal brain tissues were each homogenized in saline, drawing off the soluble material. The insoluble material was then re-extracted with a small amount of 1% SDS. Aliquots of tumor homogenate and normal brain homogenate were each linked to sepharose using CNBr activation (A). The remainder of the saline soluble GBM tumor homogenate was emulsified in complete Freund's adjuvant (CFA) and used to immunize rabbits; and the detergent fraction was used to boost the animals in incomplete Freund's adjuvant (IFA) to produce anti-GBM antiserum (B). This antiserum was passed through the GBM-sepharose column and anti-GBM antibodies were eluted off (C). To select for anti-GBM antibodies that do not bind to normal brain, the eluate was then cross-absorbed against a normal brain affinity column (D), and anti-GBM antibodies that did not bind were collected. This final antibody preparation was neutralized, concentrated, dialyzed, and biotinylated. These biotinylated antibodies were then used to screen a GBM cDNA expression library transferred to nitrocellulose filter replicas (E).

The present invention is based on the discovery that granulin is mitogenic for glial cells, and that this molecule is upregulated in various cancers of the nervous system. Moreover, the data described herein show that antibodies directed against granulin are effective in inhibiting proliferation of glial tumor cells and reducing tumor size. This invention thus provides granulin-related molecules as diagnostic and therapeutic agents for the detection, monitoring and treatment of neural cancers.

Definitions

All scientific and technical terms used in this application have meanings commonly used in the art unless otherwise specified. As used in this application, the following words or phrases have the meanings specified.

As used herein, "polypeptide" includes proteins, fragments of proteins, and peptides, whether isolated from natural sources, produced by recombinant techniques or chemically synthesized. Polypeptides of the invention typically comprise at least about 6 amino acids.

As used herein, "granulin related molecule" includes granulin polypeptides, polynucleotides encoding granulin polypeptides, polynucleotides complementary to those encoding granulin polypeptides, antibodies that specifically recognize and bind granulin polypeptides.

As used herein, "biological activity of granulin" refers to the specific binding of granulin to a granulin binding partner, such as a granulin receptor or antibody, to the expression of a granulin polynucleotide, and to the growth regulatory effects of granulin related molecules.

As used herein, "vector" means a construct, which is capable of delivering, and preferably expressing, one or more gene(s) or sequence(s) of interest in a host cell. Examples of vectors include, but are not limited to, viral vectors, naked DNA or RNA expression vectors, plasmid, cosmid or phage vectors, DNA or RNA expression vectors associated with cationic condensing agents, DNA or RNA expression vectors encapsulated in liposomes, and certain eukaryotic cells, such as producer cells.

As used herein, "expression control sequence" means a nucleic acid sequence that directs transcription of a nucleic acid. An expression control sequence can be a promoter, such as a constitutive or an inducible promoter, or an enhancer. The expression control sequence is operably linked to the nucleic acid sequence to be transcribed.

The term "nucleic acid" or "polynucleotide" refers to a deoxyribonucleotide or ribonucleotide polymer in either single- or double-stranded form, and unless otherwise limited, encompasses known analogs of natural nucleotides that hybridize to nucleic acids in a manner similar to naturally-occurring nucleotides.

As used herein, "antigen-presenting cell" or "APC" means a cell capable of handling and presenting antigen to a lymphocyte. Examples of APCs include, but are not limited to, macrophages, Langerhans-dendritic cells, follicular dendritic cells, B cells, monocytes, fibroblasts and fibrocytes. Dendritic cells are a preferred type of antigen presenting cell. Dendritic cells are found in many non-lymphoid tissues but can migrate via the afferent lymph or the blood stream to the T-dependent areas of lymphoid organs. In non-lymphoid organs, dendritic cells include Langerhans cells and interstitial dendritic cells. In the lymph and blood, they include afferent lymph veiled cells and blood dendritic cells, respectively. In lymphoid organs, they include lymphoid dendritic cells and interdigitating cells.

As used herein, "modified" to present an epitope refers to antigen-ptesenting cells (APCs) that have been manipulated to present an epitope by natural or recombinant methods. For example, the APCs can be modified by exposure to the isolated antigen, alone or as part of a mixture, peptide loading, or by genetically modifying the APC to express a polypeptide that includes one or more epitopes.

As used herein, "tumor protein" is a protein that is expressed by tumor cells. Proteins that are tumor proteins also react detectably within an immunoassay (such as an ELISA) with antisera from a patient with cancer.

An "immunogenic polypeptide," as used herein is a portion of a protein that is recognized (i.e., specifically bound) by a B-cell and/or T-cell surface antigen receptor. Such immunogenic polypeptides generally comprise at least 5 amino acid residues, more preferably at least 10, and still more preferably at least 20 amino acid residues of a protein associated with cancer or infectious disease. Certain preferred immunogenic polypeptides include peptides in which an N-terminal leader sequence and/or transmembrane domain have been deleted. Other preferred immunogenic polypeptides may contain a small N- and/or C-terminal deletion (e.g., 1–30 amino acids, preferably 5–15 amino acids), relative to the mature protein.

As used herein, "pharmaceutically acceptable carrier" includes any material which, when combined with an active ingredient, allows the ingredient to retain biological activity and is non-reactive with the subject's immune system. Examples include, but are not limited to, any of the standard pharmaceutical carriers such as a phosphate buffered saline solution, water, emulsions such as oil/water emulsion, and various types of wetting agents. Preferred diluents for aerosol or parenteral administration are phosphate buffered saline or normal (0.9%) saline.

Compositions comprising such carriers are formulated by well known conventional methods (see, for example, Remington's Pharmaceutical Sciences, Chapter 43, 14th Ed., Mack Publishing Co, Easton Pa. 18042, USA).

As used herein, "adjuvant" includes those adjuvants commonly used in the art to facilitate an immune response. Examples of adjuvants include, but are not limited to, helper peptide; aluminum salts such as aluminum hydroxide gel (alum) or aluminum phosphate; Freund's Incomplete Adjuvant and Complete Adjuvant (Difco Laboratories, Detroit, Mich.); Merck Adjuvant 65 (Merck and Company, Inc., Rahway, N.J.); AS-2 (Smith-Kline Beecham); QS-21 (Aquila Biopharmaceuticals); MPL or 3d-MPL (Corixa Corporation, Hamilton, Mont.); LEIF; salts of calcium, iron or zinc; an insoluble suspension of acylated tyrosine; acylated sugars; cationically or anionically derivatized polysaccharides; polyphosphazenes; biodegradable microspheres; monophosphoryl lipid A and quil A; muramyl tripeptide phosphatidyl ethanolamine or an immunostimulating complex, including cytokines (e.g., GM-CSF or interleukin-2, -7 or -12) and immunostimulatory DNA sequences. In some embodiments, such as with the use of a polynucleotide vaccine, an adjuvant such as a helper peptide or cytokine can be provided via a polynucleotide encoding the adjuvant.

As used herein, "a" or "an" means at least one, unless clearly indicated otherwise.

Polynucleotides of the Invention

The invention provides polynucleotides that encode one or more granulin peptides, such as granulin D (base pairs 1254–2099), or a portion or other variant thereof. Other granulin polypeptides include granulin/epithelin precursor, agrogranin, and granulins A, B and C. Preferred polynucleotides comprise at least 15 consecutive nucleotides, preferably at least 30 consecutive nucleotides and more preferably at least 45 consecutive nucleotides, that encode a portion of a granulin polypeptide. Polynucleotides that are fully complementary to any such sequences are also encompassed by the present invention. Polynucleotides may be single-stranded (coding or antisense) or double-stranded, and may be DNA genomic, cDNA or synthetic) or RNA molecules. RNA molecules include HnRNA molecules, which contain introns and correspond to a DNA molecule in a one-to-one manner, and mRNA molecules, which do not contain introns. Additional coding or non-coding sequences may, but need not, be present within a polynucleotide of the present invention, and a polynucleotide may, but need not, be linked to other molecules and/or support materials. Portions of such granulin polynucleotides can be useful as primers and probes for the amplification and detection of granulin related molecules in tissue specimens.

Polynucleotides may comprise a native sequence (i.e., an endogenous sequence that encodes a granulin polypeptide or a portion thereof) or may comprise a variant of such a sequence. Polynucleotide variants contain one or more substitutions, additions, deletions and/or insertions such that the immunogenicity of the encoded polypeptide is not diminished, relative to a native granulin protein. Variants preferably exhibit at least about 70% identity, more preferably at least about 80% identity and most preferably at least about 90% identity to a polynucleotide sequence that encodes a native granulin protein or a portion thereof Two polynucleotide or polypeptide sequences are said to be "identical" if the sequence of nucleotides or amino acids in the two sequences is the same when aligned for maximum correspondence as described below. Comparisons between two sequences are typically performed by comparing the sequences over a comparison window to identify and compare local regions of sequence similarity. A "comparison window" as used herein, refers to a segment of at least about 20 contiguous positions, usually 30 to about 75, 40 to about 50, in which a sequence may be compared to a reference sequence of the same number of contiguous positions after the two sequences are optimally aligned.

Optimal alignment of sequences for comparison may be conducted using the Megalign program in the Lasergene suite of bioinformatics software (DNASTAR, Inc., Madison, Wis.), using default parameters. This program embodies several alignment schemes described in the following references: Dayhoff, Mo. (1978) A model of evolutionary change in proteins—Matrices for detecting distant relationships. In Dayhoff, Mo. (ed.) Atlas of Protein Sequence and Structure, National Biomedical Research Foundation, Washington D.C. Vol. 5, Suppl. 3, pp. 345–358; Hein J. (1990) Unified Approach to Alignment and Phylogenes pp. 626–645 Methods in Enzymology vol. 183, Academic Press, Inc., San Diego, Calif.; Higgins, D. G. and Sharp, P. M. (1989) CABIOS 5:151–153; Myers, E. W. and Muller W. (1988) CABIOS 4:11–17; Robinson, E. D. (1971) Comb. Theor. 11:105; Santou, N., Nes, M.:(1987) Mol. Biol. Evol. 4:406–425; Sneath, P. H. A. and Sokal, R. R. (1973) Numerical Taxonomy the Principles and Practice of Numerical Taxonomy, Freeman Press, San Francisco, Calif.; Wilbur, W. J. and Lipman, D. J. (1983) Proc. Natl. Acad. Sci. USA 80:726–730.

Preferably, the "percentage of sequence identity" is determined by comparing two optimally aligned sequences over a window of comparison of at least 20 positions, wherein the portion of the polynucleotide or polypeptide sequence in the comparison window may comprise additions or deletions (i.e. gaps) of 20 percent or less, usually 5 to 15 percent, or 10 to 12 percent, as compared to the reference sequences (which does not comprise additions or deletions) for optimal alignment of the two sequences. The percentage is calculated by determining the number of positions at which the identical nucleic acid bases or amino acid residue occurs in both sequences to yield the number of matched positions, dividing the number of matched positions by the total number of positions in the reference sequence (i.e. the window size) and multiplying the results by 100 to yield the percentage of sequence identity.

Variants may also, or alternatively, be substantially homologous to a native gene, or a portion or complement thereof. Such polynucleotide variants are capable of hybridizing under moderately stringent conditions to a naturally occurring DNA sequence encoding a native stress protein (or a complementary sequence). Suitable moderate stringent conditions include prewashing in a solution of 5× SSC, 0.5% SDS, 1.0 mM EDTA (pH 8.0); hybridizing at 50° C.–65° C., 5× SSC, overnight; followed by washing twice at 65° C. for 20 minutes with each of 2×, 0.5× and 0.2× SSC containing 0.1% SDS.

It will be appreciated by those of ordinary skill in the art that, as a result of the degeneracy of the genetic code, there are many nucleotide sequences that encode a polypeptide as described herein. Some of these polynucleotides bear minimal homology to the nucleotide sequence of any native gene. Nonetheless, polynucleotides that vary due to differences in codon usage are specifically contemplated by the present invention. Further, alleles of the genes comprising the polynucleotide sequences provided herein are within the scope of the present invention. Alleles are endogenous genes that are altered as a result of one or more mutations, such as deletions, additions and/or substitutions of nucleotides. The resulting mRNA and protein may, but need not, have an altered structure or function. Alleles may be identified using standard techniques (such as hybridization, amplification and/or database sequence comparison).

Polynucleotides may be prepared using any of a variety of techniques known in the art. DNA encoding a granulin protein may be obtained from a cDNA library prepared from tissue expressing a granulin protein mRNA. Accordingly, human granulin DNA can be conveniently obtained from a cDNA library prepared from human tissue. The granulin protein-encoding gene may also be obtained from a genomic library or by oligonucleotide synthesis. Libraries can be screened with probes (such as antibodies to granulin or oligonucleotides of at least about 20–80 bases) designed to identify the gene of interest or the protein encoded by it. Screening the cDNA or genomic library with the selected probe may be conducted using standard procedures, such as those described in Sambrook et al., *Molecular Cloning: A Laboratory Manual* (New York: Cold Spring Harbor Laboratory Press, 1989). An alternative means to isolate the gene encoding granulin is to use PCR methodology (Sambrook et al., supra; Dieffenbach et al., *PCR Primer: A Laboratory Manual* (Cold Spring Harbor Laboratory Press, 1995)).

The oligonucleotide sequences selected as probes should be sufficiently long and sufficiently unambiguous that false positives are minimized. The oligonucleotide is preferably labeled such that it can be detected upon hybridization to DNA in the library being screened. Methods of labeling are well known in the art, and include the use of radiolabels, such as $^{32}$P-labeled ATP, biotinylation or enzyme labeling.

Hybridization conditions, including moderate stringency and high stringency, are provided in Sambrook et al., supra.

Polynucleotide variants may generally be prepared by any method known in the art, including chemical synthesis by, for example, solid phase phosphoramidite chemical synthesis. Modifications in a polynucleotide sequence may also be introduced using standard mutagenesis techniques, such as oligonucleotide-directed site-specific mutagenesis (see Adelman et al., DNA 2:183, 1983). Alternatively, RNA molecules may be generated by in vitro or in vivo transcription of DNA sequences encoding a stress protein, or portion thereof, provided that the DNA is incorporated into a vector with a suitable RNA polymerase promoter (such as T7 or SP6). Certain portions may be used to prepare an encoded polypeptide, as described herein. In addition, or alternatively, a portion may be administered to a patient such that the encoded polypeptide is generated in vivo (e.g., by transfecting antigen-presenting cells, such as dendritic cells, with a cDNA construct encoding a stress polypeptide, and administering the transfected cells to the patient).

Any polynucleotide may be further modified to increase stability in vivo. Possible modifications include, but are not limited to, the addition of flanking sequences at the 5' and/or 3' ends; the use of phosphorothioate or 2' O-methyl rather than phosphodiesterase linkages in the backbone; and/or the inclusion of nontraditional bases such as inosine, queosine and wybutosine, as well as acetyl- methyl-, thio- and other modified forms of adenine, cytidine, guanine, thymine and uridine.

Nucleotide sequences can be joined to a variety of other nucleotide sequences using established recombinant DNA techniques. For example, a polynucleotide may be cloned into any of a variety of cloning vectors, including plasmids, phagemids, lambda phage derivatives and cosmids. Vectors of particular interest include expression vectors, replication vectors, probe generation vectors and sequencing vectors. In general, a vector will contain an origin of replication functional in at least one organism, convenient restriction endonuclease sites and one or more selectable markers. Other elements will depend upon the desired use, and will be apparent to those of ordinary skill in the art.

Within certain embodiments, polynucleotides may be formulated so as to permit entry into a cell of a mammal, and to permit expression therein. Such formulations are particularly useful for therapeutic purposes, as described below. Those of ordinary skill in the art will appreciate that there are many ways to achieve expression of a polynucleotide in a target cell, and any suitable method may be employed. For example, a polynucleotide may be incorporated into a viral vector such as, but not limited to, adenovirus, adeno-associated virus, retrovirus, or vaccinia or other pox virus (e.g., avian pox virus). Techniques for incorporating DNA into such vectors are well known to those of ordinary skill in the art. A retroviral vector may additionally transfer or incorporate a gene for a selectable marker (to aid in the identification or selection of transduced cells) and/or a targeting moiety, such as a gene that encodes a ligand for a receptor on a specific target cell, to tender the vector target specific. Targeting may also be accomplished using an antibody, by methods known to those of ordinary skill in the art.

Other formulations for therapeutic purposes include colloidal dispersion systems, such as macromolecule complexes, nanocapsules, microspheres, beads, and lipid-based systems including oil-in-water emulsions, micelles, mixed micelles, and liposomes. A preferred colloidal system for use as a delivery vehicle in vitro and in vivo is a liposome (i.e., an artificial membrane vesicle). The preparation and use of such systems is well known in the art.

Granulin Polypeptides

Granulin polypeptides include granulin/epithelin precursor, agrogranin, and granulins A, B, C and D. Granulin polypeptides as described herein may be of any length. Additional sequences derived from the native protein and/or heterologous sequences may be present, and such sequences may, but need not, possess further peptide binding, immunogenic or antigenic properties.

Immunogenic polypeptides may generally be identified using well known techniques, such as those summarized in Paul, Fundamental Immunology, 4th ed., 663–665 (Lippincott-Raven Publishers, 1999) and references cited therein. Such techniques include screening polypeptides for the ability to react with antigen-specific antibodies, antisera and/or T-cell lines or clones. As used herein, antisera and antibodies are antigen-specific if they specifically bind to an antigen (i.e., they react with the protein in an ELISA or other immunoassay, and do not react detectably with unrelated proteins). Such antisera and antibodies may be prepared using well known techniques. An immunogenic polypeptide can be a portion of a native protein that reacts with such antisera and/or T-cells at a level that is not substantially less than the reactivity of the full length polypeptide (e.g., in an ELISA and/or T-cell reactivity assay). Such immunogenic portions may react within such assays at a level that is similar to or greater than the reactivity of the full length polypeptide. Such screens may generally be performed using methods well known to those of ordinary skill in the art, such as those described in Harlow and Lane, Antibodies: A Laboratory Manual, Cold Spring Harbor Laboratory, 1988. For example, a polypeptide may be immobilized on a solid support and contacted with patient sera to allow binding of antibodies within the sera to the immobilized polypeptide. Unbound sera may then be removed and bound antibodies detected using, for example, $^{125}$I-labeled Protein A.

A granulin polypeptide of the invention can comprise a variant of a native granulin protein. A polypeptide "variant," as used herein, is a polypeptide that differs from a native granulin protein in one or more substitutions, deletions, additions and/or insertions, such that the immunogenicity of the polypeptide is not substantially diminished. In other words, the ability of a variant to react with antigen-specific antisera may be enhanced or unchanged, relative to the native protein, or may be diminished by less than 50%, and preferably less than 20%, relative to the native protein. Such variants may generally be identified by modifying one of the above polypeptide sequences and evaluating the reactivity of the modified polypeptide with antigen-specific antibodies or antisera as described herein. Preferred variants include those in which one or more portions, such as an N-terminal leader sequence, have been removed. Other preferred variants include variants in which a small portion (e.g., 1–30 amino acids, preferably 5–15 amino acids) has been removed from the N- and/or C-terminal of the mature protein. Polypeptide variants preferably exhibit at least about 70%, more preferably at least about 90% and most preferably at least about 95% identity (determined as described above) to the identified polypeptides.

Preferably, a variant contains conservative substitutions. A "conservative substitution" is one in which an amino acid is substituted for another amino acid that has similar properties, such that one skilled in the art of peptide chemistry would expect the secondary structure and hydropathic nature of the polypeptide to be substantially unchanged. Amino acid substitutions may generally be made on the basis of similarity in polarity, charge, solubility, hydrophobicity, hydrophilicity and/or the amphipathic nature of the residues. For example, negatively charged amino acids include aspartic acid and glutamic acid; positively charged amino acids include lysine and arginine; and amino acids with uncharged polar head groups having similar hydrophilicity values include leucine, isoleucine and valine; glycine and alanine; asparagine and glutamine; and serine, threonine, phenylalanine and tyrosine. Other groups of amino acids that may represent conservative changes include: (1) ala, pro, gly, glu, asp, gln, asn, ser, thr; (2) cys, ser, tyr, thr; (3) val, ile, leu, met, ala, phe; (4) lys, arg, his; and (5) phe, tyr, trp, his. A variant may also, or alternatively, contain nonconservative changes. In a preferred embodiment, variant polypeptides differ from a native sequence by substitution, deletion or addition of five amino acids or fewer. Variants may also (or alternatively) be modified by, for example, the deletion or addition of amino acids that have mi al influence on the immunogenicity, secondary structure and hydropathic nature of the polypeptide.

Polypeptides may comprise a signal (or leader) sequence at the N-terminal end of the protein that co-translationally or post-translationaly directs transfer of the protein. The polypeptide may also be conjugated to a linker or other sequence for ease of synthesis, purification or identification of the polypeptide (e.g., poly-FEs), or to enhance binding of the polypeptide to a solid support. For example, a polypeptide may be conjugated to an immunoglobulin Fc region.

In some embodiments, the polypeptides are purified from the same subject to whom the composition will be administered. In these embodiments, it may be desirable to increase the number of tumor or infected cells. Such a scale up of cells could be performed in vitro or in vivo, using, for example, a SCID mouse system. Where the cells are scaled up in the presence of non-human cells, such as by growing a human subject's tumor in a SCID mouse host, care should be taken to purify the human cells from any non-human (e.g., mouse) cells that may have infiltrated the tumor. In these embodiments in which the composition will be administered to the same subject from whom the polypeptides are purified, it may also be desirable purify several granulin polypeptides to optimize the efficacy of a limited quantity of starting material.

Recombinant polypeptides encoded by DNA sequences as described above may be readily prepared from the DNA sequences using any of a variety of expression vectors known to those of ordinary skill in the art. Expression may be achieved in any appropriate host cell that has been transformed or transfected with an expression vector containing a DNA molecule that encodes a recombinant polypeptide. Suitable host cells include prokaryotes, yeast and higher eukaryotic cells. Preferably, the host cells employed are E. coli, yeast, insect cells or a mammalian cell line such as COS or CHO. Supernatants from suitable host/vector systems that secrete recombinant protein or polypeptide into culture media may be first concentrated using a commercially available filter. Following concentration, the concentrate may be applied to a suitable purification matrix such as an affinity matrix or an ion exchange resin. Finally, one or more reverse phase HPLC steps can be employed to further purify a recombinant polypeptide.

Portions and other variants having fewer than about 100 amino acids, and generally fewer than about 50 amino acids, may also be generated by synthetic means, using techniques well known to those of ordinary skill in the art. For example, such polypeptides may be synthesized using any of the commercially available solid-phase techniques, such as the Merrifield solid-phase synthesis method, where amino acids are sequentially added to a growing amino add chain. See Merrifield, J. Am. Chem. Soc. 85:2149–2146, 1963. Equipment for automated synthesis of polypeptides is commercially available from suppliers such as Perkin Elmer/Applied BioSystems Division (Foster City, Calif.), and may be operated according to the manufactuter's instructions.

Polypeptides can be synthesized on a Perkin Elmer/Applied Biosystems Division 430A peptide synthesizer using FMOC chemistry with HPTU (O-BenzotdiazoleN,N, N',N'-tetramethyluronium hexafluorophosphate) activation. A Gly-Cys-Gly sequence may be attached to the amino terminus of the peptide to provide a method of conjugation, binding to an immobilized surface, or labeling of the peptide. Cleavage of the peptides from the solid support may be carried out using the following cleavage mixture: trifluoroacetic acid:ethanedithiol:thioanisole:water:phenol (40:1:2:2:3). After cleaving for 2 hours, the peptides may be precipitated in cold methyl-t-butyl-ether. The peptide pellets may then be dissolved in water containing 0.1% trifluoroacetic acid (FA) and lyophilized prior to purification by C18 reverse phase HPLC. A gradient of 0%–60% acetonitrile (containing 0.1% TFA) in water may be used to elute the peptides. Following lyophilization of the pure fractions, the peptides may be characterized using electrospray or other types of mass spectrometry and by amino acid analysis.

Fusion Proteins

In some embodiments, the polypeptide is a fusion protein that comprises multiple polypeptides as described herein, or that comprises at least one polypeptide as described herein and an unrelated sequence. In some embodiments, the fusion protein comprises a granulin polypeptide and an immunogenic polypeptide. The immunogenic polypeptide can comprise, for example, all or a portion of an additional tumor protein.

Additional fusion partners can be added. A fusion partner may, for example, serve as an immunological fusion partner by assisting in the provision of T helper epitopes, preferably T helper epitopes recognized by humans. As another example, a fusion partner may serve as an expression enhancer, assisting in expressing the protein at higher yields than the native recombinant protein. Certain preferred fusion partners are both immunological and expression enhancing fusion partners. Other fusion partners may be selected so as to increase the solubility of the protein or to enable the protein to be targeted to desired intracellular compartments. Still further fusion partners include affinity tags, which facilitate purification of the protein.

Fusion proteins may generally be prepared using standard techniques, including chemical conjugation. Preferably, a fusion protein is expressed as a recombinant protein, allowing the production of increased levels, relative to a non-fused protein, in an expression system. Briefly, DNA sequences encoding the polypeptide components may be assembled separately, and ligated into an appropriate expression vector. The 3' end of the DNA sequence encoding one polypeptide component is ligated, with or without a peptide linker, to the 5' end of a DNA sequence encoding the second polypeptide component so that the reading frames of the sequences are in phase. This permits translation into a single fusion protein that retains the biological activity of both component polypeptides.

A peptide linker sequence may be employed to separate the first and the second polypeptide components by a distance sufficient to ensure that each polypeptide folds into its secondary and tertiary structures. Such a peptide linker sequence is incorporated into the fusion protein using standard techniques well known in the art. Suitable peptide linker sequences may be chosen based on the following factors: (1) their ability to adopt a flexible extended conformation; (2) their inability to adopt a secondary structure that could interact with functional epitopes on the first and second polypeptides; and (3) the lack of hydrophobic or charged residues that might react with the polypeptide functional epitopes. Preferred peptide linker sequences contain Gly, Asn and Ser residues. Other near neutral amino acids, such as Thr and Ala may also be used in the linker sequence. Amino acid sequences which may be usefully employed as linkers include those disclosed in Maratea et al., Gene 40:39–46, 1985; Murphy et al., Proc. Natl. Acad. Sci. USA 83:8258–8262, 1986; U.S. Pat. No. 4,935,233 and U.S. Pat. No. 4,751,180. The linker sequence may generally be from 1 to about 50 amino acids in length. Linker sequences are not required when the first and second polypeptides have non-essential N-terminal amino acid regions that can be used to separate the functional domains and prevent steric interference.

The ligated DNA sequences are operably linked to suitable transcriptional or translational regulatory elements. The regulatory elements responsible for expression of DNA are located 5' to the DNA sequence encoding the first polypeptides. Similarly, stop codons required to end translation and transcription termination signals are present 3' to the DNA sequence encoding the second polypeptide.

Fusion proteins are also provided that comprise a polypeptide of the present invention together with an unrelated immunogenic protein. Preferably the immunogenic protein is capable of eliciting a memory response. Examples of such proteins include tetanus, tuberculosis and hepatitis proteins (see, for example, Stoute et al., New Engl. J. Med. 336:86–91, 1997).

Within preferred embodiments, an immunological fusion partner is derived from protein D, a surface protein of the gram-negative bacterium Haemophilus influenza B (WO 91/18926). Preferably, a protein D derivative comprises approximately the first third of the protein (e.g., the first N-terminal 100–110 amino acids), and a protein D derivative may be lipidated. Within certain preferred embodiments, the first 109 residues of a Lipoprotein D fusion partner is included on the N-terminus to provide the polypeptide with additional exogenous T-cell epitopes and to increase the expression level in E. coli (thus functioning as an expression enhancer). The lipid tail ensures optimal presentation of the antigen to antigen presenting cells. Other fusion partners include the non-structural protein from influenzae virus, NS I (hemaglutinin). Typically, the N-terminal 81 amino acids are used, although different fragments that include T-helper epitopes may be used.

In another embodiment, the immunological fusion partner is the protein known as LYTA, or a portion thereof (preferably a C-terminal portion). LYTA is derived from *Streptococcus pneumoniae*, which synthesizes an N-acetyl-L-alanine amidase known-as amidase LYTA (encoded by the LytA gene; Gene 43:265–292, 1986). LYTA is an autolysin that specifically degrades certain bonds in the peptidoglycan backbone. The C-terminal domain of the LYTA protein is responsible for the affinity to the choline or to some choline analogues such as DEAR This property has been exploited for the development of E. coli C-LYTA expressing plasmids useful for expression of fusion proteins. Purification of hybrid proteins containing the C-LYTA fragment at the amino terminus has been described (see Biotechnology 10:795–798, 1992). Within a preferred embodiment, a repeat portion of LYTA may be incorporated into a fusion protein. A repeat portion is found in the C-terminal region starting at residue 178. A particularly preferred repeat portion incorporates residues 188–305.

In general, polypeptides (including fusion proteins) and polynucleotides as described herein are isolated. An "isolated" polypeptide or polynucleotide is one that is removed from its original environment. For example, a naturally occurring protein is isolated if it is separated from some or all of the coexisting materials in the natural system. Preferably, such polypeptides are at least about 90% pure, more preferably at least about 95% pure and most preferably at least about $^{99}$% pure. A polynucleotide is considered to be isolated if, for example, it is cloned into a vector that is not a part of the natural environment.

Antibodies

The term "antibody" is used in the broadest sense and specifically covers single anti-granulin monoclonal antibodies (including agonist, antagonist and neutralizing antibodies) and anti-granulin antibody compositions with poly-epitopic specificity. The term "monoclonal antibody" (mAb) as used herein refers to an antibody obtained from a population of substantially homogeneous antibodies, i.e. the antibodies comprising the individual population are identical except for possible naturally-occurring mutations that may be present in minor amounts.

The invention provides antibodies that bind to granulin proteins and polypeptides. The most preferred antibodies will specifically bind to a granulin protein and will not bind (or will bind weakly) to non-granulin proteins and polypeptides. Anti-granulin antibodies that are particularly contemplated include monoclonal and polyclonal antibodies as well as fragments containing the antigen binding domain and/or one or more complementarity determining regions of these antibodies. As used herein, an antibody fragment is defined as at least a portion of the variable region of the immunoglobulin molecule that binds to its target, i.e., the antigen binding region.

Granulin antibodies of the invention may be particularly useful in neural cancer diagnostic and prognostic assays, and imaging methodologies. Intracellularly expressed antibodies (e.g., single chain antibodies) may be therapeutically useful in treating cancers in which the expression of granulin is involved, such as for example advanced and metastatic brain cancers. Also useful in therapeutic methods for treatment of neural cancer are systemically administered granulin antibodies that interfere with granulin function or that target cells expressing granulin for delivery of a toxin or therapeutic molecule. Such delivery of a toxin or therapeutic molecule can be achieved using known methods of conjugating a second molecule to the granulin antibody or fragment thereof. Similarly, such antibodies may be useful in the treatment, diagnosis, and/or prognosis of other cancers, to the extent granulin is also expressed or overexpressed in other types of cancer.

The invention also provides various immunological assays useful for the detection and quantification of granulin polypeptides. Such assays generally comprise one or more granulin antibodies capable of recognizing and binding a granulin, and may be performed within various immunological assay formats well known in the art, including but not limited to various types of radioimmunoassays, enzyme-linked immunosorbent assays (ELISA), enzyme-linked immunofluorescent assays (ELIFA), and the like. In addition, immunological imaging methods capable of detecting cancers expressing granulin are also provided by the invention, including but not limited to radioscintigraphic imaging methods using labeled granulin antibodies. Such assays may be clinically useful in the detection, monitoring, and prognosis of granulin expressing cancers.

Various methods for the preparation of antibodies are well known in the art. For example, antibodies may be prepared by immunizing a suitable mammalian host using a granulin protein, peptide, or fragment, in isolated or immunoconjugated form (Antibodies: A Laboratory Manual, CSH Press, Eds., Harlow, and Lane (1988); Harlow, Antibodies, Cold Spring Harbor Press, NY (1989)). In addition, fusion proteins of granulin may also be used, such as a granulin GST-fusion protein. In another embodiment, a granulin peptide may be synthesized and used as an immunogen.

The antibodies or fragments may also be produced, using current technology, by recombinant means. Regions that bind specifically to the desired regions of the granulin protein can also be produced in the context of chimeric or CDR grafted antibodies of multiple species origin. Humanized or human granulin antibodies may also be produced and are preferred for use in therapeutic contexts. Methods for humanizing mutine and other non-human antibodies by substituting one or more of the non-human antibody CDRs for corresponding human antibody sequences are well known (see for example, Jones et al., 1986, Nature 321: 522–525; Riechmann et al., 1988, Nature 332: 323–327; Verhoeyen et al., 1988, Science 239: 1534–1536). See also, Carter et al., 1993, Proc. Natl. Acad. Sci. USA 89: 4285 and Sims et al., 1993, J. Immunol. 151: 2296. Methods for producing fully human monoclonal antibodies include phage display and transgenic methods (for review, see Vaughan et al., 1998, Nature Biotechnology 16: 535–539).

Fully human granulin monoclonal antibodies may be generated using cloning technologies employing large human Ig gene combinatorial libraries (i.e., phage display) (Griffiths and Hoogenboom, Building an in vitro immune system: human antibodies from phage display libraries. In: Protein Engineering of Antibody Molecules for Prophylactic and Therapeutic Applications in Man. Clark, M. (Ed.), Nottingham Academic, pp 45–64 (1993); Burton and Barbas, Human Antibodies from combinatorial libraries. Id., pp 65–82). Fully human granulin monoclonal antibodies may also be produced using transgenic mice engineered to contain human immunoglobulin gene loci as described in PCT Patent Application WO98/24893, Kucherlapati and Jakobovits et al., published Dec. 3, 1997 (see also, Jakobovits, 1998, Exp. Opin. Invest. Drugs 7(4): 607–614). This method avoids the in vitro manipulation required with phage display technology and efficiently produces high affinity authentic human antibodies.

Reactivity of granulin antibodies with a granulin protein may be established by a number of well known means, including western blot, immunoprecipitation, ELISA, and FACS analyses using, as appropriate, granulin proteins, peptides, granulin-expressing cells or extracts thereof A granulin antibody or fragment thereof of the invention may be labeled with a detectable marker or conjugated to a second molecule. Suitable detectable markers include, but are not limited to, a radioisotope, a fluorescent compound, a bioluminescent compound, chemiluminescent compound, a metal chelator or an enzyme. A second molecule for conjugation to the granulin antibody can be selected in accordance with the intended use. For example, for therapeutic use, the second molecule can be a toxin or therapeutic agent. Further, bi-specific antibodies specific for two or more granulin epitopes may be generated using methods generally known in the art. Homodimeric antibodies may also be generated by cross-linking techniques known in the art (e.g., Wolff et al., Cancer Res. 53: 2560–2565).

T Cells

Immunotherapeutic compositions may also, or alternatively, comprise T cells specific for a granulin polypeptide. Such cells may generally be prepared in vitro or ex vivo, using standard procedures. For example, T cells may be isolated from bone marrow, peripheral blood, or a fraction of bone marrow or peripheral blood of a patient, using a commercially available cell separation system, such as the ISOLEX™ magnetic cell selection system, available from Nexell Therapeutics, Irvine, Calif. (see also U.S. Pat. No. 5,536,475); or MACS cell separation technology from Miltenyi Biotec, including Pan T Cell Isolation Kit, CD4+ T Cell Isolation Kit, and CD8+ T Cell Isolation Kit (see also U.S. Pat. No. 5,240,856; U.S. Pat. No. 5,215,926; WO 89/06280; WO 91/16116 and WO 92/07243). Alternatively, T cells may be derived from related or unrelated humans, non-human mammals, cell lines or cultures.

T cells may be stimulated with a granulin polypeptide, polynucleotide encoding a granulin polypeptide and/or an antigen presenting cell (APC) that expresses such a granulin polypeptide. The stimulation is performed under conditions and for a time sufficient to permit the generation of T cells that are specific for the polypeptide. Preferably, a granulin polypeptide or polynucleotide is present within a delivery vehicle, such as a microsphere, to facilitate the generation of specific T cells.

T cells are considered to be specific for a granulin polypeptide if the T cells kill target cells coated with the polypeptide or expressing a gene encoding the polypeptide. T cell specificity may be evaluated using any of a variety of standard techniques. For example, within a chromium release assay or proliferation assay, a stimulation index of more than two fold increase in lysis and/or proliferation, compared to negative controls, indicates T cell specificity. Such assays may be performed, for example, as described in Chen et al., Cancer Res. 54:1065–1070, 1994.

Detection of the proliferation of T cells may be accomplished by a variety of known techniques. For example, T cell proliferation can be detected by measuring an increased rate of DNA synthesis (e.g., by pulse-labeling cultures of T cells with tritiated thymidine and measuring the amount of tritiated thymidine incorporated into DNA). Contact with a stress protein complex (100 ng/ml–100 μg/ml, preferably 200 ng/ml–25 μg/ml) for 3–7 days should result in at least a two fold increase in proliferation of the T cells. Contact as described above for 2–3 hours should result in activation of the T cells, as measured using standard cytokine assays in which a two fold increase in the level of cytokine release (e.g., TNF or IFN-γ) is indicative of T cell activation (see Coligan et al., Current Protocols in Immunology, vol. 1, Wiley Interscience (Greene 1998)). T cells that have been activated in response to a stress polypeptide, polynucleotide or polypeptide-expressing APC may be CD4+ and/or CD8+. T cells can be expanded using standard techniques.

Within preferred embodiments, the T cells are derived from either a patient or a related, or unrelated, donor and are administered to the patient following stimulation and expansion. For therapeutic purposes, CD4+ or CD8+ T cells that proliferate in response to a granulin polypeptide, polynucleotide or APC can be expanded in number either in vitro or in vivo. Proliferation of such T cells in vitro may be accomplished in a variety of ways. For example, the T cells can be re-exposed to a granulin polypeptide, with or without the addition of T cell growth factors, such as interleukin-2, and/or stimulator cells. Alternatively, one or more T cells that proliferate in the presence of a granulin polypeptide can be expanded in number by cloning. Methods for cloning cells are well known in the art, and include limiting dilution.

Pharmaceutical Compositions and Vaccines

The invention provides granulin polypeptide, polynucleotides, T cells and/or antigen presenting cells that are incorporated into pharmaceutical compositions, including immunogenic compositions (i.e., vaccines). Pharmaceutical compositions comprise one or more such compounds and, optionally, a physiologically acceptable carrier. Vaccines may comprise one or mote such compounds and an adjuvant that serves as a non-specific immune response enhancer. The adjuvant may be any substance that enhances an immune response to an exogenous antigen. Examples of adjuvants include conventional adjuvants, biodegradable microspheres (e.g., polylactic galactide), immunostimulatory oligonucleotides and liposomes (into which the compound is incorporated; see e.g., Fullerton, U.S. Pat. No. 4,235,877). Vaccine preparation is generally described in, for example, M. F. Powell and M. J. Newman, eds., "Vaccine Design (the subunit and adjuvant approach)," Plenum Press (NY, 1995). Pharmaceutical compositions and vaccines within the scope of the present invention may also contain other compounds that may be biologically active or inactive. For example, one or more immunogenic portions of other tumor antigens may be present, either incorporated into a fusion polypeptide or as a separate compound, within the composition or vaccine.

A pharmaceutical composition or vaccine can contain DNA encoding one or more of the polypeptides as described above, such that the polypeptide is generated in situ. As noted above, the DNA may be present within any of a variety of delivery systems known to those of ordinary skill in the art, including nucleic acid expression systems, bacteria and viral expression systems. Numerous gene delivery techniques are well known in the art, such as those described by Rolland, Crit. Rev. Therap. Drug Carrier Systems 15:143–198, 1998, and references cited therein. Appropriate nucleic acid expression systems contain the necessary DNA sequences for expression in the patient (such as a suitable promoter and terminating signal). Bacterial delivery systems involve the administration of a bacterium (such as *Bacillus-Calmette-Guemn*) that expresses an immunogenic portion of the polypeptide on its cell surface or secretes such an epitope.

In a preferred embodiment, the DNA may be introduced using a vital expression system (e.g., vaccinia or other pox virus, retrovirus, or adenovirus), which may involve the use of a non-pathogenic (defective), replication competent virus. Suitable systems are disclosed, for example, in Fisher-Hoch et al., Proc. Natl. Acad. Sci. USA 86:317–321, 1989; Flexner et al., Ann. N. Y. Acad Sci. 569:86–103, 1989; Flexner et al., Vaccine 8:17–21, 1990; U.S. Pat. Nos. 4,603,112, 4,769,330, and 5,017,487; WO 89/01973; U.S. Pat. No. 4,777,127; GB 2,200,651; EP 0,345,242; WO 91/02805; Berkner-Biotechniques 6:616–627, 1988; Rosenfeld et al., Science 252: 431–434, 1991; Kolls et al., Proc. Nad. Acad. Sci. USA 91:215–219, 1994; Kass-Eisler et al., Proc. Natl. Acad. Sci. USA 90:11498–11502, 1993; Guzman et al., Circulation 88:2838–2848, 1993; and Guzman et al., Cir. Res. 73:1202–1207, 1993. Techniques for incorporating DNA into such expression systems are well known to those of ordinary skill in the art. The DNA may also be "naked," as described, for example, in Ulmer et al., Science 259:1745–1749, 1993 and reviewed by Cohen, Science 259:1691–1692, 1993. The uptake of naked DNA may be increased by coating the DNA onto biodegradable beads, which are efficiently transported into the cells.

While any suitable carrier known to those of ordinary skill in the art may be employed in the pharmaceutical compositions of this invention, the type of carrier will vary depending on the mode of administration. Compositions of the present invention may be formulated for any appropriate manner of administration, including for example, topical, oral, nasal, intravenous, intracranial, intraperitoneal, subcutaneous or intramuscular administration. For parenteral administration, such as subcutaneous injection, the carrier preferably comprises water, saline, alcohol, a fat, a wax or a buffer. For oral administration, any of the above carriers or a solid carrier, such as mannitol, lactose, starch, magnesium stearate, sodium saccharine, talcum, cellulose, glucose, sucrose, and magnesium carbonate, may be employed. Biodegradable microspheres (e.g., polylactate polyglycolate) may also be employed as carriers for the pharmaceutical compositions of this invention. Suitable biodegradable microspheres are disclosed, for example, in U.S. Pat. Nos. 4,897,268 and 5,075,109.

Such compositions may also comprise buffers (e.g., neutral buffered saline or phosphate buffered saline), carbohydrates (e.g., glucose, mannose, sucrose or dextrans), mannitol, proteins, polypeptides or amino acids such as glycine, antioxidants, chelating agents such as EDTA or glutathione, adjuvants (e.g., aluminum hydroxide) and/or preservatives. Alternatively, compositions of the present invention may be formulated as a lyophilizate. Compounds may also be encapsulated within liposomes using well known technology.

Any of a variety of adjuvants may be employed in the vaccines of this invention. Most adjuvants contain a substance designed to protect the antigen from rapid catabolism, such as aluminum hydroxide or mineral oil, and a stimulator of immune responses, such as lipid A, *Bortadella pertussis* or *Mycobacterium tuberculosis* derived proteins. Suitable adjuvants are commercially available as, for example, Freund's Incomplete Adjuvant and Complete Adjuvant (Difco Laboratories, Detroit, Mich.); Merck Adjuvant 65 (Merck and Company, Inc., Rahway, N.J.); aluminum salts such as aluminum hydroxide gel (alum) or aluminum phosphate; salts of calcium, iron or zinc; an insoluble suspension of acylated tyrosine acylated sugars; cationically or anionically derivatized polysaccharides; polyphosphazenes biodegradable microspheres; monophosphoryl lipid A and quil A. Cytokines, such as GM CSF or interleukin-2, -7, or -12, may also be used as adjuvants.

Within the vaccines provided herein, the adjuvant composition is preferably designed to induce an immune response predominantly of the Th1 type. High levels of Th1-type cytokines (e.g., IFN-α, IL-2 and IL-12) tend to favor the induction of cell mediated immune responses to an administered antigen. In contrast, high levels of Th2-type cytokines (e.g., IL-4, IL-5, IL-6, IL-10 and TNF-β) tend to favor the induction of humoral immune responses. Following application of a vaccine as provided herein, a patient will support an immune response that includes Th1- and Th2-type responses. Within a preferred embodiment, in which a response is predominantly Th1-type, the level of Th1-type cytokines will increase to a greater extent than the level of Th2-type cytokines. The levels of these cytokines may be readily assessed using standard assays. For a review of the families of cytokines, see Mosmann and Coffman, Ann. Rev. Immunol. 7:145–173, 1989.

The compositions described herein may be administered as part of a sustained release formulation (i.e., a formulation such as a capsule or sponge that effects a slow release of compound following administration). Such formulations may generally be prepared using well known technology and administered by, for example, oral, rectal or subcutaneous implantation, or by implantation at the desired target site, such as a site of surgical excision of a tumor. Sustained-release formulations may contain a polypeptide, polynucleotide or antibody dispersed in a carrier matrix and/or contained within a reservoir surrounded by a rate controlling membrane. Carriers for use within such formulations are biocompatible, and may also be biodegradable; preferably the formulation provides a relatively constant level of active component release. The amount of active compound contained within a sustained release formulation depends upon the site of implantation, the rate and expected duration of release and the nature of the condition to be treated or prevented.

Antigen Presenting Cells

Any of a variety of delivery vehicles may be employed within pharmaceutical compositions and vaccines to facilitate production of an antigen-specific immune response that targets tumor cells. Delivery vehicles include antigen presenting cells (APCs), such as dendritic cells, macrophages, B cells, monocytes and other cells that may be engineered to be efficient APCs. Such cells may, but need not, be genetically modified to increase the capacity for presenting the antigen, to improve activation and/or maintenance of the T cell response, to have anti-tumor or anti-infective effects per se and/or to be immunologically compatible with the receiver (i.e., matched BLA haplotype). APCs may generally be isolated from any of a variety of biological fluids and organs, including tumor and petitumoral tissues, and may be autologous, allogeneic, syngeneic or xenogeneic cells.

Certain-preferred embodiments of the present invention use dendritic cells or progenitors thereof as antigen-presenting cells. Dendritic cells ate highly potent APCs (Banchereau and Steinman, Nature 392:245–251, 1998) and have been shown to be effective as a physiological adjuvant for eliciting prophylactic or therapeutic antitumor immunity (see Timmerman and Levy, Ann. Rev. Med. 50:507–529, 1999). In general, dendritic cells may be identified based on their typical shape (stellate in situ, with marked cytoplasmic processes (dendrites) visible in vitro) and based on the lack of differentiation markers of B cells (CD19 and CD20), T cells (CD3), monocytes (CD14) and natural killer cells (CD56), as determined using standard assays. Dendritic cells may, of course, be engineered to express specific cell surface receptors or ligands that are not commonly found on dendritic cells in vivo or ex vivo, and such modified dendritic cells are contemplated by the present invention. As an alternative to dendritic cells, secreted vesicles antigen-loaded dendritic cells (called exosomes) may be used within a vaccine (see Zitvogel et al., Nature Med. 4:594–600, 1998).

Dendritic cells and progenitors may be obtained from peripheral blood, bone marrow, tumor-infiltrating cells, peritumoral tissues-infiltrating cells, lymph nodes, spleen, skin, umbilical cord blood or any other suitable tissue or fluid. For example, dendritic cells may be differentiated ex vivo by adding a combination of cytokines such as GM-CSF, IL-4, IL-13 and/or TNFα to cultures of monocytes harvested from peripheral blood. Alternatively, CD34 positive cells harvested from peripheral blood, umbilical cord blood or bone marrow may be differentiated into dendritic cells by adding to the culture medium combinations of GM-CSF, IL-3, TNFα, CD40 ligand, LPS, flt3 ligand and/or other compound(s) that induce maturation and proliferation of dendritic cells.

Dendritic cells are conveniently categorized as "immature" and "mature" cells, which allows a simple way to discriminate between two well characterized phenotypes. However, this nomenclature should not be construed to exclude all possible intermediate stages of differentiation. Immature dendritic cells are characterized as APC with a high capacity for antigen uptake and processing, which correlates with the high expression of Fcγ receptor, mannose receptor and DEC-205 marker. The mature phenotype is typically characterized by a lower expression of these markers, but a high expression of cell surface molecules responsible for T cell activation such as class I and class II NMC, adhesion molecules (e.g., CD54 and CD11) and costimulatory molecules (e.g., CD40, CD80 and CD86).

APCs may generally be transfected with a polynucleotide encoding a granulin polypeptide (or portion or other variant thereof) such that the granulin polypeptide, or an immunogenic portion thereof, is expressed on the cell surface. Such transfection may take place ex vivo, and a composition or vaccine comprising such transfected cells may then be used for therapeutic purposes, as described herein. Alternatively, a gene delivery vehicle that targets a dendritic or other antigen presenting cell may be administered to a patient, resulting in transfection that occurs in vivo. In vivo and ex vivo transfection of dendritic cells, for example, may generally be performed using any methods known in the art, such as those described in WO 97/24447, or the gene gun approach described by Mahvi et al., Immunology and Cell Biology 75:456–460, 1997. Antigen loading of dendritic cells may be achieved by incubating dendritic cells or progenitor cells with the stress polypeptide, DNA (naked or within a plasmid vector) or RNA; or with antigen-expressing recombinant bacterium or viruses (e.g., vaccinia, fowlpox, adenovirus or lentivirus vectors). Prior to loading, the polypeptide may be covalently conjugated to an immunological partner that provides T cell help (e.g., a carrier molecule). Alternatively, a dendritic cell may be pulsed with a non-conjugated immunological partner, separately or in the presence of the polypeptide.

Therapeutic and Prophylactic Methods

Treatment includes prophylaxis and therapy. Prophylaxis or therapy can be accomplished by a single direct injection at a single time point or multiple time points to a single or multiple sites. Administration can also be nearly simultaneous to multiple sites. Patients or subjects include mammals, such as human, bovine, equine, canine, feline, porcine, and ovine animals. The subject is preferably a human.

A cancer may be diagnosed using criteria generally accepted in the art, including the presence of a malignant tumor. Pharmaceutical compositions and vaccines may be administered either prior to or following surgical removal of primary tumors and/or treatment such as administration of radiotherapy or conventional chemotherapeutic drugs.

Within certain embodiments, immunotherapy may be active immunotherapy, in which treatment relies on the in vivo stimulation of the endogenous host immune system to react against tumors or infected cells with the administration of immune response-modifying agents (such as polypeptides and polynucleotides disclosed herein).

Within other embodiments, immunotherapy may be passive immunotherapy, in which treatment involves the delivery of agents with established tumor-immune reactivity (such as effector cells or antibodies) that can directly or indirectly mediate antitumor effects and does not necessarily depend on an intact host immune system. Examples of effector cells include T cells as discussed above, T lymphocytes (such as CD8+ cytotoxic T lymphocytes and CD4+ T-helper tumor-infiltrating lymphocytes), killer cells (such as Natural Killer cells and lymphokine-activated killer cells), B cells and antigen-presenting cells (such as dendritic cells and macrophages) expressing a polypeptide provided herein. In a preferred embodiment, dendritic cells are modified in vitro to present the polypeptide, and these modified APCs are administered to the subject. T cell receptors and antibody receptors specific for the polypeptides recited herein may be cloned, expressed and transferred into other vectors or effector cells for adoptive immunotherapy. The polypeptides provided herein may also be used to generate antibodies or anti-idiotypic antibodies (as described above and in U.S. Pat. No. 4,918,164) for passive immunotherapy.

Administration and Dosage

The compositions are administered in any suitable manner, often with pharmaceutically acceptable carriers. Suitable methods of administering cells in the context of the present invention to a subject are available, and, although more than one route can be used to administer a particular cell composition, a particular route can often provide a more immediate and more effective reaction than another route.

The dose administered to a patient, in the context of the present invention, should be sufficient to effect a beneficial therapeutic response in the patient over time, or to inhibit disease progression. Thus, the composition is administered to a subject in an amount sufficient to elicit an effective immune response to the specific antigens and/or to alleviate, reduce, cure or at least partially arrest symptoms and/or complications from the disease. An amount adequate to accomplish this is defined as a "therapeutically effective dose."

Routes and frequency of administration of the therapeutic compositions disclosed herein, as well as dosage, will vary from individual to individual, and may be readily established using standard techniques. In general, the pharmaceutical compositions and vaccines may be administered, by injection (e.g., intracutaneous, intratumoral, intramuscular, intravenous or subcutaneous), intranasally (e.g., by aspiration) or orally. Preferably, between 1 and 10 doses may be administered over a 52 week period. Preferably, 6 doses are administered, at intervals of 1 month, and booster vaccinations may be given periodically thereafter. Alternate protocols may be appropriate for individual patients. In one embodiment, 2 intradermal injections of the composition are administered 10 days apart.

A suitable dose is an amount of a compound that, when administered as described above, is capable of promoting an anti-tumor immune response, and is at least 10–50% above the basal (i.e., untreated) level. Such response can be monitored, for example, by measuring the anti-tumor antibodies in a patient or by vaccine-dependent generation of cytolytic effector cells capable of killing the patient's tumor cells in vitro. Such vaccines should also be capable of causing an immune response that leads to an improved clinical outcome (e.g., more frequent remissions, complete or partial or longer disease-free survival) in vaccinated patients as compared to nonvaccinated patients. In general, for pharmaceutical compositions and vaccines comprising one or more polypeptides, the amount of each polypeptide present in a dose ranges from about 100 μg to 5 mg per kg of host. Suitable volumes will vary with the size of the patient, but will typically range from about 0.1 mL to about 5 mL.

In general, an appropriate dosage and treatment regimen provides the active compound(s) in an amount sufficient to provide therapeutic and/or prophylactic benefit. Such a response can be monitored by establishing an improved clinical outcome (e.g., more frequent remissions, complete or partial, or longer disease-free survival) in treated patients as compared to non-treated patients. Increases in preexisting immune responses to a tumor protein generally correlate with an improved clinical outcome. Such immune responses may generally be evaluated using standard proliferation, cytotoxicity or cytokine assays, which may be performed using samples obtained from a patient before and after treatment.

Additional Methods

The invention provides a method for detecting cancer in a neural tissue comprising contacting the tissue with a molecule that recognizes and binds a granulin molecule. The molecule can be, for example, an antibody directed against a granulin peptide, or an antisense nucleotide directed against a granulin nucleic acid molecule. The tissue can be from a mammal, such as human, bovine, equine, canine, feline, porcine, and ovine tissue. The tissue is preferably a human. The tissue can comprise a tumor specimen, cerebrospinal fluid, or other suitable specimen. In one embodiment, the method comprises use of an ELISA type assay that employs a granulin antibody to detect the presence of granulin in a specimen. Those skilled in the art will appreciate additional variations suitable for the method of detecting cancer in neural tissue through detection of a granulin molecule in a specimen. This method can also be used to monitor granulin levels in neural tissue of a patient undergoing treatment for a neural cancer. The suitability of a granulin-targeted therapeutic regimen for initial or continued treatment can be determined by monitoring granulin levels using this method.

The invention additionally provides a method for identifying a molecule that inhibits proliferation of neural cancer cells. The method comprises contacting a candidate molecule with a granulin molecule and determining whether the candidate molecule disrupts the biological activity of the granulin molecule. Disruption of the biological activity of the granulin molecule is indicative of a molecule that inhibits proliferation of neural cancer cells. Representative granulin molecules include antibodies, proteins and nucleotides.

The invention provides a method for identifying differentially expressed gene products that are translated from mRNA species, using antibody-based screening of a cDNA expression library. This method, termed differential immuno-absorption (DIA), can be coupled to cDNA microarray hybridization and used in the identification of genes that play a role in the malignant progression of cancer. The method for identifying proteins differentially expressed in a target tissue comprises linking a target tissue homogenate to a first substrate, and passing an antiserum raised against the target tissue homogenate over the first substrate to elute antibodies that bind the target tissue. The method further comprises linking a control tissue homogenate to a second substrate, and passing the eluted antibodies over the second substrate to obtain target antibodies that bind proteins present in the target tissue and not proteins present in the control tissue. The target antibodies so obtained are then used to screen a nucleic acid expression library containing proteins expressed in the target tissue. Proteins bound by the target antibodies are identified as differentially expressed in the target tissue. The invention thereby provides novel proteins, antibodies and nucleotides identified by this method.

In addition, the invention provides a method of identifying a protein that is differentially expressed in a neural cancer comprising screening a first library of cells associated with neural cancer and a second library of non-tumor neural cells with a nucleic acid molecule encoding a candidate protein. Increased hybridization of the nucleic acid molecule with the first library relative to the second library is indicative of a protein that is differentially expressed in neural cancer. In one embodiment, the screening comprises a cDNA microarray assay.

EXAMPLES

The following examples are presented to illustrate the present invention and to assist one of ordinary skill in making and using the same. The examples are not intended in any way to otherwise limit the scope of the invention.

Example 1

Identification of Proteins by Differential Immuno-Absorption

This example describes a method for identifying differentially expressed gene products that are actually translated from mRNA species, using antibody-based screening of a cDNA expression library. This method, termed differential immuno-absorption (DIA), can be coupled to cDNA microarray hybridization and used in the identification of genes that play a role in the malignant progression of cancer. The differential expression of granulin in brain tumors was discovered by this method.

Materials & Methods

Differential Immuno-Absorption. Glioblastoma multiforme (GBM) tumor tissue from a human patient was immediately snap frozen in liquid nitrogen at the time of surgery. Non-tumor brain was obtained from a surgical resection for trauma and similarly frozen. Both tissue specimens were homogenized in phosphate-bufferedsaline (PBS, pH=7.0) with a glass mortar and pestle. The soluble material was aspirated, and the insoluble material was re-extracted into a second fraction using 0.1% sodium dodecyl sulfate (SDS). Both fractions were used for affinity purification and immunizations. Affinity chromatography was carried out using an aliquot of extracted material immobilized on cyanogen bromide (CNBr)-activated Sepharose 4B columns (Pharmacia) according to manufacturer's specifications. The immobilized GBM tumor tissue extract was loaded into a fritted column (Varian), blocked with 1 M glycine, precycled with 0.1 M HCl, and neutralized with 0.1 M borate-buffered saline (BBS, pH=8.4). The extract of non-tumor brain tissue was also similarly immobilized.

Antisera were raised against the GBM tumor homogenate by subcutaneous and intramuscular immunization of New Zealand White (NZW) rabbits using complete and incomplete Freund's adjuvants. Several bleeds were collected from two animals, pooled, and diluted 1:2 with 0.1 M borate-buffered saline (pH=8.4). The diluted antiserum was passed over the GBM affinity column, and unbound material was washed off with BBS. Bound material was eluted off using glycine buffers adjusted to pH=3, pH=2, and then pH=1. The effluent and eluate were monitored at 280 nm (LKB), and the antiserum was passed repeatedly through the column until depleted. The eluate was then collected into BBS, checked for neutral pH, and cross-absorbed repeatedly (until depleted of cross-reactive antibodies) against the column of non-tumor brain to select out antibodies that may bind normal brain antigens. The unbound material was further cross-absorbed against normal human plasma to select out non-specific antibodies. The final product was concentrated using YM30 columns (Aricon) and dialyzed into carbonate buffer (pH=9.5). The antibodies were biotinylated at a molar ratio of 15:1 using NHS long-chain biotin (Sigma) and repurified using a column of G-25 (Pharmacia). These biotinylated antibodies were then used to screen a glioblastoma phagemid cDNA expression library.

Construction and Screening of cDNA Expression Library. For construction of the glioblastoma cDNA expression library, a human glioblastoma multiforme tumor was snap frozen in liquid nitrogen at the time of surgery and retained at −80° C. Total RNA was extracted from 500 mg of fresh frozen tumor tissue using Trizol reagent per manufacturer's protocol (Gibco-BRL). Messenger RNA from 30 μg total RNA was isolated using double chromatography on oligo-dT cellulose columns (Gibco-BRL). Double-stranded cDNA was synthesized from this mRNA using a Superscript II cDNA synthesis kit (Gibco-BRL), and the cDNAs were ligated into a λ ZipLox phagemid vector (Gibco-BRL). We obtained a library titer estimated at $5.0 \times 10^6$ plaque-forming units (PFU). Approximately $2.0 \times 10^6$ PFUs were plated and grown in the presence of isopropyl-1-thio-β-D-galactoside (IPTG), lifted onto nitrocellulose membranes, and incubated with biotinylated anti-GBM antibodies (1:1000 dilution). The membranes were then incubated with streptavidin-HRP and diarinobenzidine tetrahydrochloride (Pierce). Positive clones were isolated, re-screened, and subcloned into the pZL1 plasmid vector (Gibco-BRL) by in vivo excision. Inserts were verified by agarose gel electrophoresis and partially sequenced using a dsDNA cycle sequencing kit (Gibco-BRL) per manufacturer's protocol.

Microarray of Cloned DIA Products. After cloning the subtractive products into the pZL1 vector, plasmid inserts were PCR amplified using vector-specific primers. PCR was performed in 50 μl reactions containing 10 mM Tris (pH 9.0), 50 mM KCl, 0.1% gelatin, 2.5 U Taq DNA polymerase and 150 μM dNTP. Thermal cycling conditions consisted of an initial denaturation at 94° C. for 2 min, followed by 35 cycles of 94° C. for 1 min, 68° C. for 1 min and 72° C. for 1.5 min, with a final 72° C. extension for 10 min, in a PTC100 thermal cycler (MJ Research). Five microliters of each PCR amplification product were examined by agarose gel electrophoresis with ethidium bromide staining. A single band was detected in 26 of the 28 PCR reactions performed. Each of the 26 successfully amplified PCR products (1–2 μg) was recovered from the remaining 45 μg of each PCR reaction by ethanol precipitation.

The PCR products were arrayed onto glass slides, following a protocol similar to that previously described (18). Briefly, the PCR products were resuspended in 15 μl 1× standard saline citrate (SSC). A custom-built arraying robot picked up approximately 600 nl DNA solution and deposited 1–4 nl DNA solution in duplicate onto a silanized glass slide surface (Sigma). After printing, the slide was hydrated for 10 s over a 37° C. water bath, snap dried for 2 s on a 100° C. heating block, then UV cross-linked with 4000 mJ short wave irradiation (Stratagene Stratalinker). The slide was then washed for 2 min sequentially in 0.2% SDS and distilled water. The bound DNA was denatured in distilled water at 100° C., desiccated in an ice-cold bath of 95% ethanol, and air-dried.

Probe labeling, microarray hybridization, and washes were performed as described previously (19). mRNA from a large batch of pooled tumor and non-tumor brain specimens was used to make cDNA labeled with Cy5. The Cy5-labeled cDNA from this collective batch served as the common reference probe in all hybridizations. mRNA samples (2 μg) from 10 individual tumor and non-tumor brain specimens (e.g., 8 gliomas and 2 normal brain tissues) were used to make cDNA labeled with Cy-3.

After hybridization with the arrayed subtractive clones, Cy-3 and Cy-5 intensities were scanned using a custom-built two-color laser scanning fluorimeter. The image files were analyzed with custom-written software that performed quantification similar to that previously published (20, 21). Relative abundance of each of our 26 subtractive clones (L1–L26) in tumor versus normal brain was calculated using the equation: [(Cy3 signal–Cy3 background)tumor/(Cy5 signal–Cy5 background)] divided by [(Cy3 signal–Cy3 background)normal/(Cy5 signal–Cy5 background)].

Northern Blot Analysis of Granulin mRNA Expression. Tissue total RNA was extracted using Trizol reagent (Gibco-BRL) per manufacturer's instructions, and 10 μg/lane were separated on 1.2% denaturing agarose gels, transferred overnight to Hybond membranes (Amersham) using 10× SSC, and irreversibly fixed by UV cross-linking. Prehybridization and hybridization were performed at 65° C. in ExpressHyb solution (Clontech). 32P-labeled cDNA probes were generated from our plasmid DNA containing granulin cDNA using random primers per manufacturer's protocol (NEB). After hybridization, membranes were washed (2× SSC plus 0.1% SDS at 37° C. for 20 min, followed by 0.2× SSC plus 0.1% SDS at 61° C. for 20 min), and exposed to X-ray film (Kodak) at 80° C. Blots were then stripped with 0.1% SDS at 100° C. for 15 minutes and re-probed with 32P-labeled ribosomal 18S cDNA in order to control for gel loading and RNA integrity.

In situ Hybridization of Granulin mRNA Expression. In situ hybridization was performed using $^{35}$S-labeled riboprobes following previously published protocols (22). Briefly, surgically resected human brain tissues (tumor and non-tumor) were rapidly frozen in isopentane directly from the operating room. Frozen tissues were sectioned on a cryostat at 20 μm thickness, post-fixed in 4% paraformaldehyde, washed, and stored at −75° C. Sections were washed, acetylated, defatted, and incubated with $^{35}$S-labeled sense or antisense granulin cRNA probe (107 cpm/ml) at 60° C. overnight (18–24 h). Following RNAse A (20 μ/ml) treatment at 45° C., sections were washed in descending concentrations of SSC, air dried, and dipped for emulsion autoradiography in Kodak NTB2 (1:1 dilution). Following exposure to emulsion for 5 weeks, the slides were developed and counterstained with hematoxylin and eosin.

Hybridization densities were measured from the in situ slides by counting silver grains within representative cells using an image analysis computer (Olympus microscope and MCID Imaging software; Imaging Research, Inc.) (23). Sections through several different tumor and non-tumor human brain specimens that had been hybridized with granulin cRNA were chosen for counts. Briefly, two independent observers outlined labeled regions within each slide, and the computer determined the optical density and quantity of silver grains within each outlined area. Ten measurements were performed for each slide and averaged into single values per mm$^2$ per specimen. These values were then divided by the estimated number of cells per mm$^2$ for each specimen to get the average units of silver grains per cell. The average quantity of silver grains per cell for each tumor was compared to that of non-tumor brain specimens using the Student's t-test.

Results

Isolation of Glioblastoma-Associated Gene Products by DIA. Using differential immuno-absorption (DIA), positive reactions were found in 28 plaques. Positive clones were isolated, subcloned into the pZL1 plasmid vector by in vivo excision, and partially sequenced. BLAST analysis of these sequences revealed 19 novel clones and 9 genes contained in the GenBank database. Of the 9 known clones that were identified by our DIA technique, 2 are known to regulate growth, 1 codes for a chemotherapy resistance protein, and 2 regulate gene expression (Table 1). Of the 19 novel sequences that were identified, Northern blot analyses were performed on 9 of these cDNAs and differential expression was confirmed in tumor tissues versus normal brain in all nine of the clones tested.

TABLE 1

Brain tumor-associated gene products identified by differential immuno-absorption (DIA). From the 28 cDNAs that were identified by this method, 9 represented genes with sequence homology to known genes in the GenBank database. Shown below are the clone number and the known or putative function of each gene product

| Clone | GenBankID | Function |
|---|---|---|
| L2, L6 | Human GFAP | Glial fibrillary acidic protein; expressed in astrocytes; used as marker for gliomas |
| L5 | Human granulin | Peptide isolated from human granulocytes; autocrine growth factor for teratoma-derived PC cells; mitogen for 3T3 fibroblasts |
| L9 | GAPDH | Glyceraldehyde-3-phosphate dehydrogenase; glycolytic enzyme; increased in lung cancer; putative role in apoptosis and neurodegenerative diseases |
| L10 | Carbonyl reductase | Enzyme involved in chemotherapy resistance and free radical modulation |
| L19 | DNA-dependent ATPase (putative) & X-linked nuclear protein | Helicase involved in transcription initiation and brain differentiation (putative) |
| L20 | Homologous with tyrosine kinases | Unknown |

TABLE 1-continued

Brain tumor-associated gene products identified by differential immuno-absorption (DIA). From the 28 cDNAs that were identified by this method, 9 represented genes with sequence homology to known genes in the GenBank database. Shown below are the clone number and the known or putative function of each gene product

Figure 2:
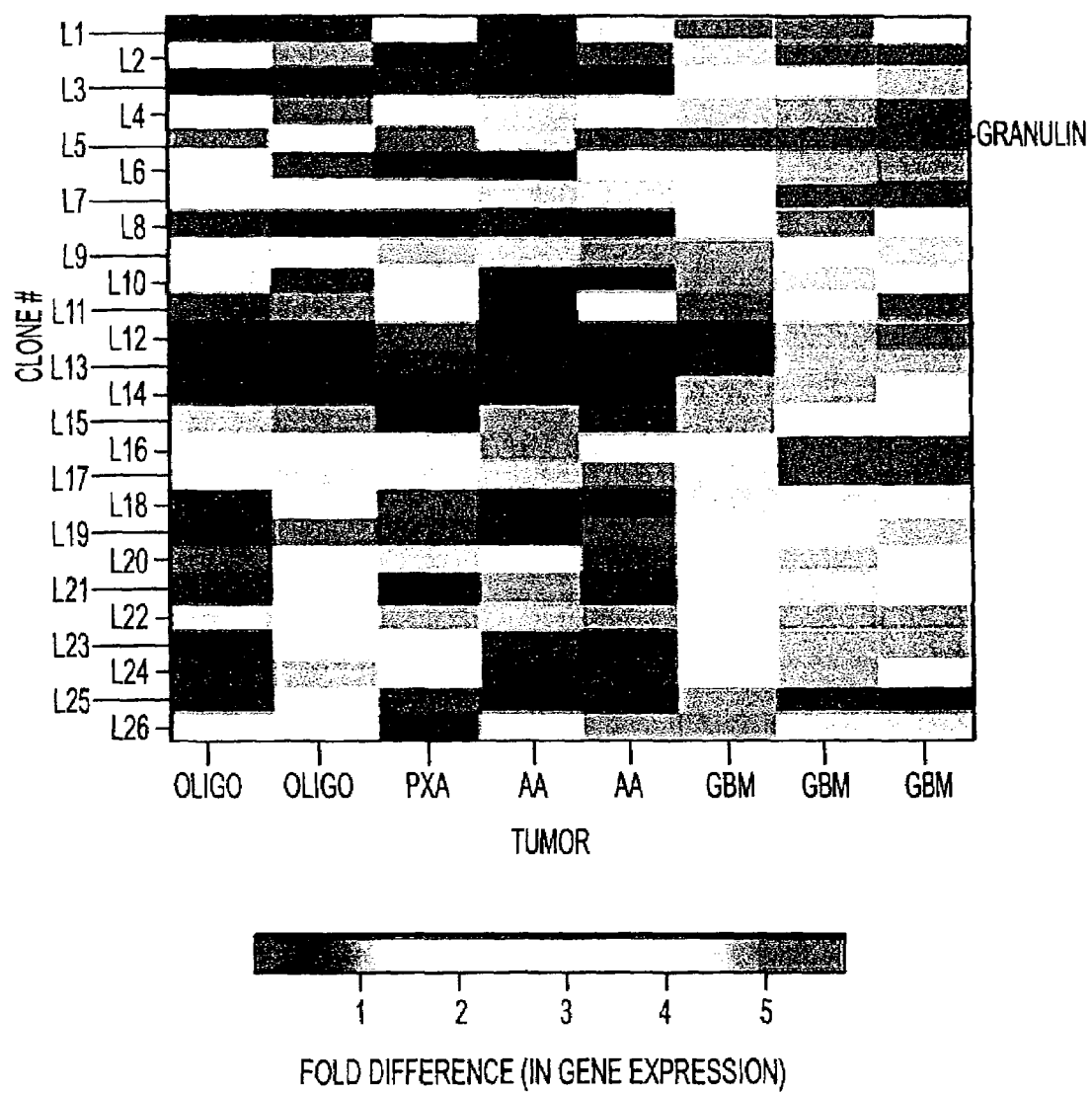
FIG. 2 shows cDNA microarray analysis of clones identified using differential immuno-absorption (DIA). A total of 26 DIA genes (rows) were analyzed in duplicate in this experiment. The expression pattern of each gene is displayed here as a horizontal strip. For each clone (L1 through L26), the ratio of mRNA levels in various brain tumors versus its level in non-tumor brain tissue is represented by a color, according to the color scale at the bottom. Note that the L5 clone (granulin) showed consistently high levels of expression in all the brain tumor tissues analyzed, (3× to 30× that of normal brain). GBM=glioblastoma; AA=anaplastic astrocytoma; PXA=pleomorphic xanthoastrocytoma; Oligo=oligodendroglioma.

| Clone | GenBankID | Function |
| --- | --- | --- |
| L24 | Hsa2 mitochondrial cytochrome | Unknown |
| L25 | Osteopontin | Ligand for integrin; involved in adhesion, migration, & osteoclastogenesis | cDNA Microarray Analysis of DIA products. To perform high-capacity screening of DIA clones in multiple tumor and non-tumor brain tissues, cDNA microarray analysis was used (18, 20, 21). Twenty-six of the 28 plasmid inserts isolated were successfully PCR amplified using vector-specific primers which amplify the inserted fragment from the pZL1 vector. Each PCR product was then arrayed onto glass slides and hybridized with two-color fluorophore-labeled probes in a manner similar to that already published (19). The cDNA made from each sample of tumor or normal brain mRNA was labeled with the fluorescent dye Cy3 (green) and mixed with a common reference probe labeled with a second fluorescent dye, Cy5 (red). Using this high throughput arrayer, the relative abundance of each of the 26 DIA clones in 8 different brain tumor samples compared to non-tumor brain tissue was determined (FIG. 2). As seen in FIG. 2, for the majority of the 26 genes tested, the three glioblastoma samples analyzed appeared to have higher levels of differential expression than the other tumor types. Furthermore, analysis of the expression of these candidate tumor-specific genes revealed that one of the isolated clones, L5, had consistently much higher levels of expression in gliomas compared to normal brain (three- to thirty-fold).

This differentially expressed clone, L5, was therefore chosen for further characterization. The 590 base pair cDNA of clone L5 was manually sequenced and found to be identical to the human granulin/epithelin precursor. Granulins (also known as epithelins) are cysteine-rich polypeptides that have growth factor-like activity. They represent a relatively new class of growth regulators, first described in 1990, with possible roles in inflammation and tumorigenesis (27, 28). The granulin gene exists as a single copy in the human genome on chromosome 17 (29). It is widely expressed in epithelial and tumorigenic cell lines in vitro, many of which respond to the gene product by enhanced cell proliferation, suggesting an autocrine or paracrine role for these factors (30–32). Several of the known structural and biological properties of the granulins resemble those of the epidermal growth factor (EGF)-like proteins (33–35). It is unclear whether this is physiologically significant, as the in vivo expression and function of granulin have not yet been well defined.

Granulin mRNA Expression in Human Gliomas. The differential expression of granulin in human gliomas was confirmed by Northern blot analysis, which showed a transcript of 2.1 kb expressed in 86% (18/21) of human gliomas and 0% (0/3) of the non-tumor brain tissues analyzed (FIG. 3A). Interestingly, of the three gliomas that had absence of any granulin signal, one was from a patient that had received previous radiation therapy and one was from a low-grade oligodendroglioma. These data suggest that granulin expression may be mitigated by radiation and/or related to higher malignancy and tumor progression.

To better appreciate the potential role of this gene product, it would be essential to know the extent to which it is expressed within other human tissues. To determine this, radiolabeled granulin cDNA was used to probe Northern blots of a variety of peripheral organs. The probe hybridized predominantly to a 2.1-kb transcript in human testes, spleen, and kidney after 2 weeks of exposure, but not to all other human tissues tested, including normal brain, lung, heart, skeletal muscle, pancreas, liver, and adrenal gland (FIG. 3B).

Differential expression of granulin mRNA was also seen in tumor versus non-tumor tissues using in situ hybridization. Granulin antisense riboprobe hybridized predominantly to hypercellular areas of tumor tissue (FIGS. 4A and 4B). The identity of these cells labeled by in situ hybridization was supported by counterstaining the tissue sections with hemotoxylin and eosin, which revealed that the majority of the RNA was within tumor cells and not in the tissue stroma (FIGS. 4C and 4D). Sense strand riboprobe cDNA was used as a control and showed no specific labeling, indicating that the cellular hybridization obtained with the antisense probe was specific for the granulin mRNA. Quantitation of granulin hybridization densities was measured from the in situ slides using image analysis software. This analysis revealed significantly greater numbers of silver grains within cells of the most malignant brain tumors (e.g., anaplastic astrocytomas and glioblastoma multiforme) compared to non-tumor glial cells (p=0.006), confirming that elevated levels of granulin mRNA ate expressed in high-grade primary brain tumors (Table 2).

TABLE 2

Relative quantitation of in situ hybridization of granulin mRNA in normal brain and primary brain tumors.

| Tissue | Number of silver grains/mm$^2$ | Average number of silver grains/cell |
| --- | --- | --- |
| Normal brain (n = 2) | 50 | 1.6 |
|  | 160 | 5.3 |
| Pilocytic Astrocytoma (n = 3) | 3800 | 9.6 |
|  | 3900 | 7.3 |
|  | 4500 | 7.7 |
| Oligodendroglioma (n = 2) | 9,500 | 20.2 |
|  | 17,000 | 21.2 |
| Anaplastic astrocytoma (n = 2) | 17,000 | 29.7 |
|  | 22,000 | 15.2 |
| Glioblastoma multiforme (n = 3) | 20,000 | 25.9 |
|  | 27,000 | 32.3 |
|  | 30,000 | 53.6 |

Discussion

In summary, the detection and characterization of a putative growth factor differentially expressed in brain tumors versus non-tumor brain tissue demonstrates the usefulness of the DIA technique for identification of subtractive tissue-specific gene products that may have significant biological activity. The DIA method described here is an alternative to currently established methods for the purposes of identifying differences in gene expression. It has the advantage of selecting for gene products that are actually translated from mRNA species, which can readily be cloned and synthesized for use in functional assays as described herein. Furthermore, because this technique is based on the generation of subtractive antibodies used to screen cDNA expression libraries, antibodies to clones of interest can be generated for antibody-based studies. These results demonstrate the potential of this technique to identify candidate glioma-associated peptides that readily allow study of expression patterns and biological function.

With current microarray technology, it is feasible to screen relatively large numbers of tumor samples for the expression of subtractive products. This allows easy discrimination of redundant clones and rapid confirmation of truly differentially expressed genes. Although only 26 clones were isolated and cloned from this example of the DIA method, it is conceivable that thousands of differentially expressed gene products could be identified among the approximately 15,000 individual mRNA species in a pair of human cell populations (i.e., tumor versus normal). This is based on the assumption that perhaps 15% of the estimated 100,000 genes in the human genome are expressed in any individual cell type at a particular time (41). Even if thousands of differential clones are generated from the subtractive approach of the invention, current robotic microarray technology allows for the fabrication of arrays containing up to 20,000 distinct cDNA targets (18). The expression of these thousands of targets can be monitored in multiple tissue samples, just as the relative expression of 26 clones were measured in various brain tumor tissues. Thus, microarrays in concert with subtractive gene hunting methods could serve as useful tools for the identification of biologically intriguing and clinically relevant human gene sequences.

Using the combination of DIA and microarray hybridization, a putative oncogene, granulin D, with a likely function in glial cell proliferation, was identified. This granulin peptide belongs to a family of putative growth factors that have previously been characterized by a unique structural motif and implicated in growth regulation (28, 30, 31, 33–35). Structurally, granulins consist of 12 cysteines with four cysteine pairs flanked by two single cysteines at both the amino and the carboxyl termini (26, 42). The predicted protein architecture consists of four stacked β-hairpins, each connected to the next with two parallel disulfide bridges, and a peptide backbone arranged as two ladders in a left-handed super-helix (34). Interestingly, this tertiary structure is partially homologous to that of epidermal growth factor (EGF). Granulin proteins have been shown to have mitogenic activity in murine embryonic 3T3 cells, in the tumorigenic teratoma-derived PC cell line, in human epithelial and fibroblastic cells, and in murine keratinocytes (27, 30, 33, 35). The data disclosed herein show growth regulatory effects of this peptide in primary rat astrocytes and in early-passage human glioblastoma cell lines.

The surprising parallels between the granulin and EGF systems are of interest. Given that amplification of the epidermal growth factor receptor (EGF-R) gene is one of the most common findings in glioblastomas and malignant astrocytomas (1, 43), it is intriguing that one of the glioblastoma-associated clones identified via the DIA technique may be related to the EGF/EGF-R system. Nevertheless, there are many molecules that have EGF-like domains, and other investigators have found that granulin does not bind to wild-type EGF-R (also called erbB-1) (44). Furthermore, Western blot analysis of EGF-R expression in the human glioblastomas used in the bioassay disclosed herein revealed EGF-R overexpression in only one of the three tumors tested, with no direct correlation between EGF-R overexpression and granulin-induced growth regulation. Interestingly, however, all three of the tumors studied had overexpression of the closely related EGFR-like transmembrane receptor tyrosine kinase erbB-2 (also called HER-2 or neu).

Also intriguing in this context is the fact that both granulin and erbB-2 are genes located on chromosome 17 (29, 45). Previous reports in the literature have found that high-grade gliomas have over-representation of chromosome 7 and gain of chromosome 17q at the cytogenetic level (46, 47), which presumably relates to amplification of EGF-R and erbB-2 at the gene expression level (48–50). Although overexpression of erbB-2 has been found in a subset of primary brain tumors, its putative ligand in brain cancers is not yet known. It would be interesting to determine whether tumors with amplification of chromosome 17q have coordinate overexpression of erbB-2 and granulin, which may support the idea of granulin being a ligand for the erbB-2 proto-oncogene autocrine/paracrine loop. Given the tissue-specificity of granulin for tumor versus normal brain, its EGF-like domains, its location on chromosome 17, and its implicated role in glial cell growth regulation, it is conceivable that this gene product may be a useful target for the development of new therapeutics for malignant brain tumors.

Example 2

Regulation of Astrocyte and Glioblastoma Cell Proliferation by Granulin Peptide and Granulin Antibody This example describes the effects of granulin peptide and a granulin antibody on the proliferation of astrocytes in primary culture and of cultured human glioblastoma cells. The results show that granulin is mitogenic for astrocytes and glioblastoma cells, and that the growth of these cells can be inhibited by treatment with a polyclonal antibody directed against granulin.

Materials & Methods

Cell cultures. Primary cultures of rat astrocytes from the brains of adult Fischer 344 rats were isolated following a protocol previously described (24). Cultures were maintained in Dulbecco's modified Eagle's medium (DMEM, Gibco-BRL) supplemented with 10% fetal bovine serum (FBS), L-glutamine, and antibiotic drugs (100 U/ml penicillin and 100 µg/ml streptomycin) at 37° C. in 5% $CO_2$.

Primary human glioblastoma cells cultures were established using a protocol similar to that previously published (25). Tumors were taken directly from the operating room at the time of surgery. Tissues were finely minced using sterile scissors, rinsed with PBS, and dispersed with trypsin-EDTA. Monolayer cells were plated in T75 flasks (Costar) and cultured in DMEM/Ham's F12 (Irvine Scientific) supplemented with 10% FBS (Gibco-BRL), L-glutamine, and antibiotics (100 U/ml penicillin and 100 µg/ml streptomycin).

Measurement of Cell Proliferation. The effect of granulin D peptide and granulin antibody on the proliferation of primary tat astrocytes and three early-passage human glioblastoma cell lines were examined. Synthetic peptide, consisting of the 55-amino acid sequence of granulin D (26), was provided by Research Genetics. For the antibody studies, a polyclonal antibody was raised against this 55-amino acid synthetic peptide conjugated to KLH. The IgG fraction was isolated from sera using protein-A sepharose (Zymed), concentrated using a Centri-cell concentrator (Amicon), and stored in borate buffer consisting of 25 mM sodium borate, 100 mM boric acid, 75 mM NaCl, and 5 mM EDTA.

The biological effects of increasing concentrations of granulin D peptide and antibody on in vivo cell growth rates were assayed using 3H-thymidine incorporation. Cells were grown to about 60% confluence in T75 flasks (Costar) and then plated in 12-well plates (Corning) at a density of 104 cells per well in 1 ml of DMEM supplemented with 10% FBS. One day after plating, the medium was removed and replaced with medium containing increasing concentrations of either synthetic granulin D peptide (0 ng/ml to 1000 ng/ml) or granulin D antibody (1:1000 to 1:100) in triplicate. Three days later, the medium was again replaced by fresh medium and supplemented with increasing amounts of peptide or antibody. After three days, 0.5 µCi/well of 3H-thymidine was added for overnight incubation at 37° C. Wells were then washed twice with 1 ml of ice-cold phosphate-buffered saline (PBS) and collected by treatment with trypsin-EDTA. Cell suspensions were transferred to scintillation vials and radioactivity counted with a scintillation counter. Six separate experiments were performed on each cell line, using triplicate wells per experiment (n=18). The Student's t-test was used to interpret the significance of differences between groups.

Results

In vitro Growth Regulation of Glial Cells by Granulin D. Four granulins, A, B, C, and D, have previously been isolated from human inflammatory cell exudates (28, 33, 36, 37). Each is a small protein of approximately 6 kDa that is derived from a larger precursor of 593 amino acids, known as acrogranin (38–40). The acrogranin cDNA (clone L5) isolated from human glioblastomas contained the entire sequence for granulin D (base pairs 1254 to 2099). (26).

Figure 5A:
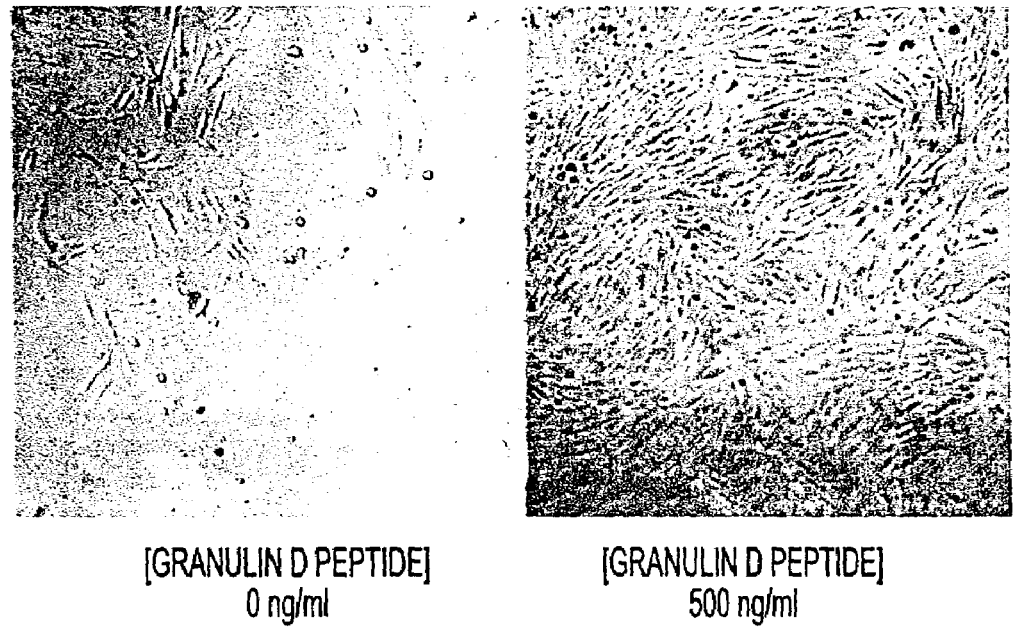
FIGS. 5A–D shows growth regulatory effects of granulin D in rat and human glial cell lines. (A) Photomicrographs of cell cultures of primary rat astrocytes without (left, 0 ng/well) and with (tight, 500 ng/well) addition of synthetic granulin D peptide. Original magnification=100×. (B) Dose-response graph of granulin D peptide on the proliferation of rat astrocytes. Addition of purified synthetic granulin D to culture media stimulated DNA synthesis of primary rat astrocyte cells up to 300% of controls as measured by standard $^3$H-thymidine incorporation assays, with ED$_{50}$=6 ng/well. (C) Dose-response graph of granulin D peptide on the proliferation of human glioblastoma cells. (D) Growth suppressive effect of granulin D antibody in human glioblastoma cell cultures. Results were normalized in terms of percentage of control proliferation, with the control cells receiving equal volumes of heat-inactivated antibody or borate buffer (without antibody). For the human cell culture experiments (C and D), three different human glioblastoma cell lines were studied. For all studies, the controls were set to 100% and all other counts in each experiment were normalized to this value. The results shown are combined from six separate experiments, using triplicate wells each. Bars represent mean values ±SD.
Figure 5B:
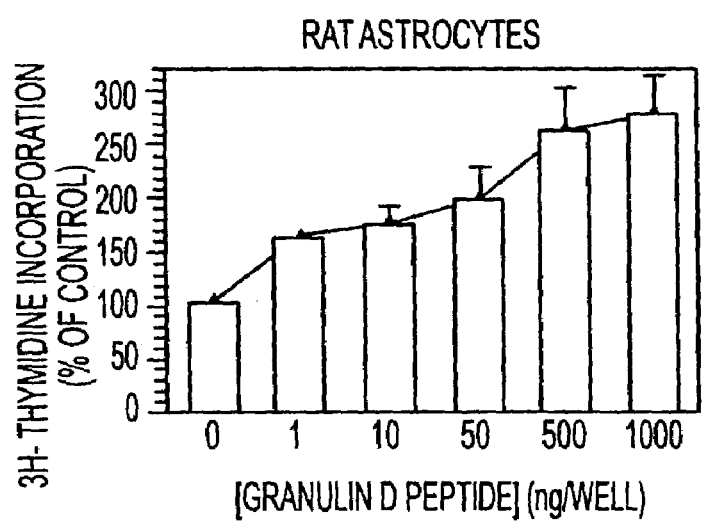
Figure 5C:
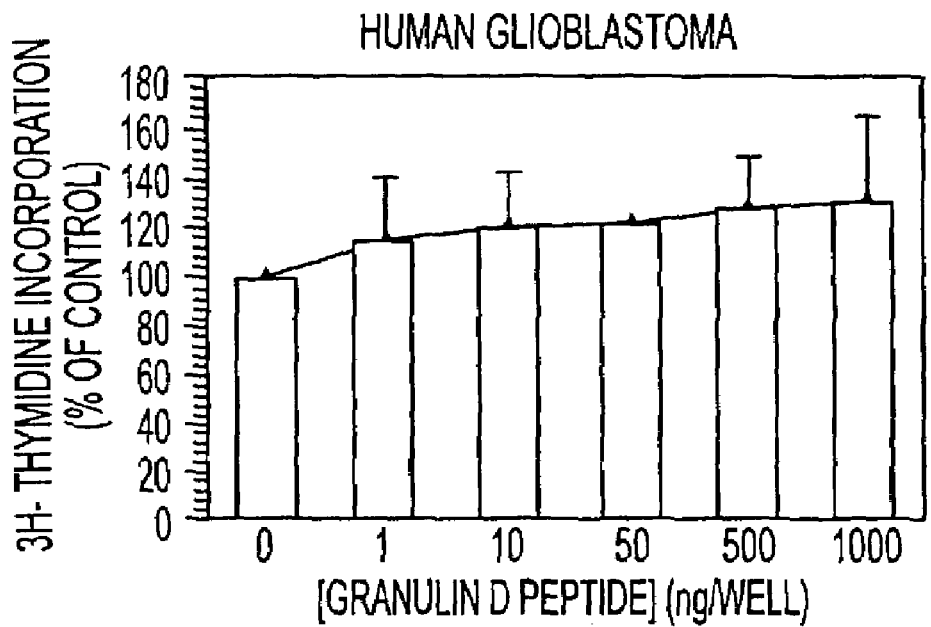

The implication of granulin molecules in growth regulation with a tertiary structure reminiscent of that of EGF suggested a potentially important role for the L5/granulin D clone as a putative growth factor. In order to determine if granulin D may modulate glial cell proliferation, a 55-amino acid peptide corresponding to the known sequence of granulin D was synthesized (26). The effect of this synthetic peptide on proliferation rates of rat astrocytes in culture was then studied using a standard $^3$H-thymidine incorporation assay. As shown in FIG. 5, addition of synthetic granulin D peptide stimulated DNA synthesis of rat astrocytes in vitro up to 300% in a dose-dependent manner (FIGS. 5A and 5B). Statistically significant increases in cell proliferation (up to 150% of controls) were seen with the addition of as little as 1 ng/ml (169 pM) of granulin D to cell culture (p=0.025). Interestingly, this synthetic peptide had a much more modest effect on the proliferation of primary human glioblastoma cells in culture, showing only a 120–150% increase (p=0.068) in growth with the addition of over 1000 ng/ml (169 nM) of granulin D (FIG. 5C). This may be explained by the fact that these human cells were tumotous and already expressed high levels of granulin (as shown by Northern blot and in situ hybridization). Thus, the putative receptors of this potential autocrine growth factor may be saturated by endogenous granulin and thereby preclude further growth stimulation by the addition of exogenous peptide.

Figure 5D:
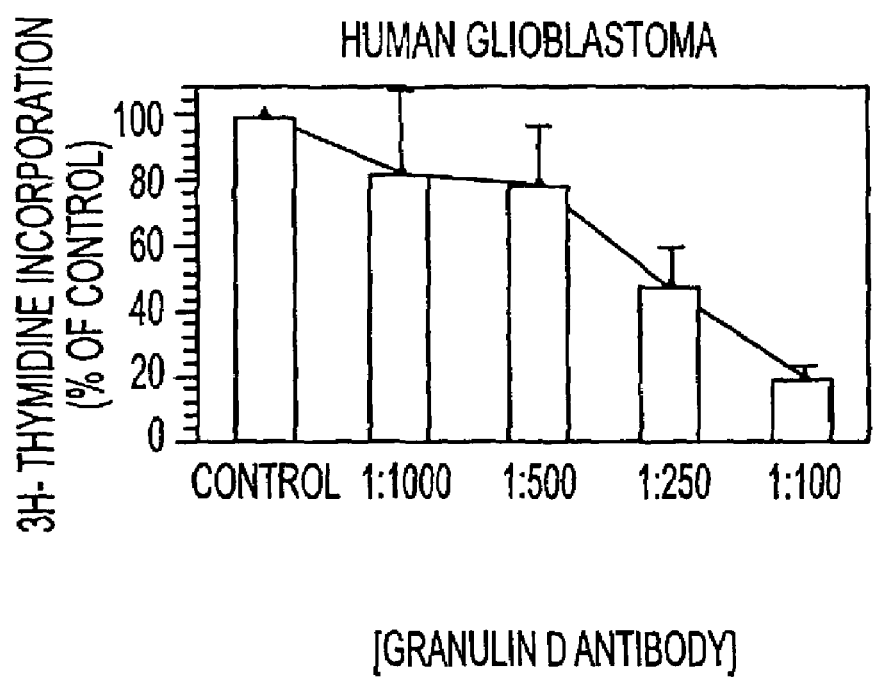

To further evaluate the growth regulatory role of granulin D on human tumor cells in vitro, a polyclonal antibody was raised against the 55-amino acid granulin D peptide and assayed for its ability to inhibit cell proliferation in three primary human glioblastoma cultures. As shown in FIG. 5D, the addition of increasing concentrations of purified granulin D antibody to early-passage human brain tumor cell cultures significantly inhibited cell growth in vitro. $^3$H-thymidine incorporation was suppressed down to only 18.6% of controls with the highest concentration of antibody tested (1:100 dilution, p=0.035).

Example 3

In Vivo Reduction of Tumor Volume with Granulin Antibody Therapy

Figure 6:
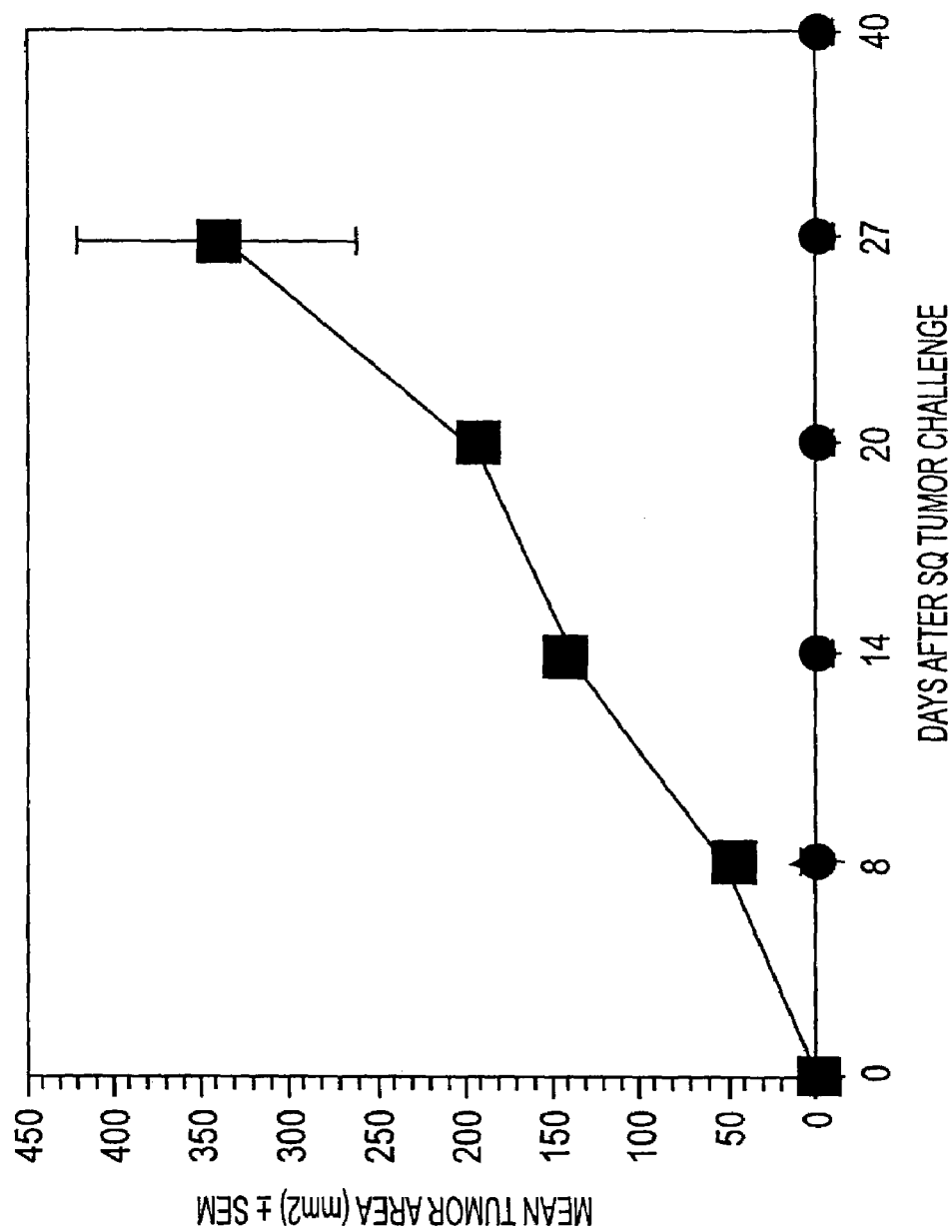
FIG. 6 is a graph showing the size (mean tumor area in mm$^2$) of subcutaneous (s.c. or "SQ") U87 human glioblastoma tumors in CD1 nu/nu mice treated with anti-granulin antibody as a function of days after subcutaneous tumor challenge. Circles represent mice treated with anti-granulin antibody (n=10) and squares represent mice treated with dPBS (n=8).

In this example, an affinity-purified polyclonal antibody was raised against the 55-aa granulin D peptide conjugated to keyhole limpet hemocyanin (KLH). Nude (nu/nu) mice were challenged with $10^6$ U87 human glioblastoma tumor cells and treated i.p. with 500 µg of anti-granulin antibody (in a volume of 500 µl dPBS) or dPBS alone, starting one day after tumor challenge and every other day thereafter for 21 days. Injection of dPBS alone failed to protect mice against s.q. tumor growth. Treatment with anti-granulin antibody, however, protected 100% of the mice from tumor growth for up to 40 days, as shown in FIG. 6. These results demonstrate that molecules that interfere with the biological activity of granulin can be an effective therapeutic in the treatment of neural tumors.

Example 4

Prolonged Survival of Tumor-bearing Mice with Granulin Antibody Therapy

Figure 7:
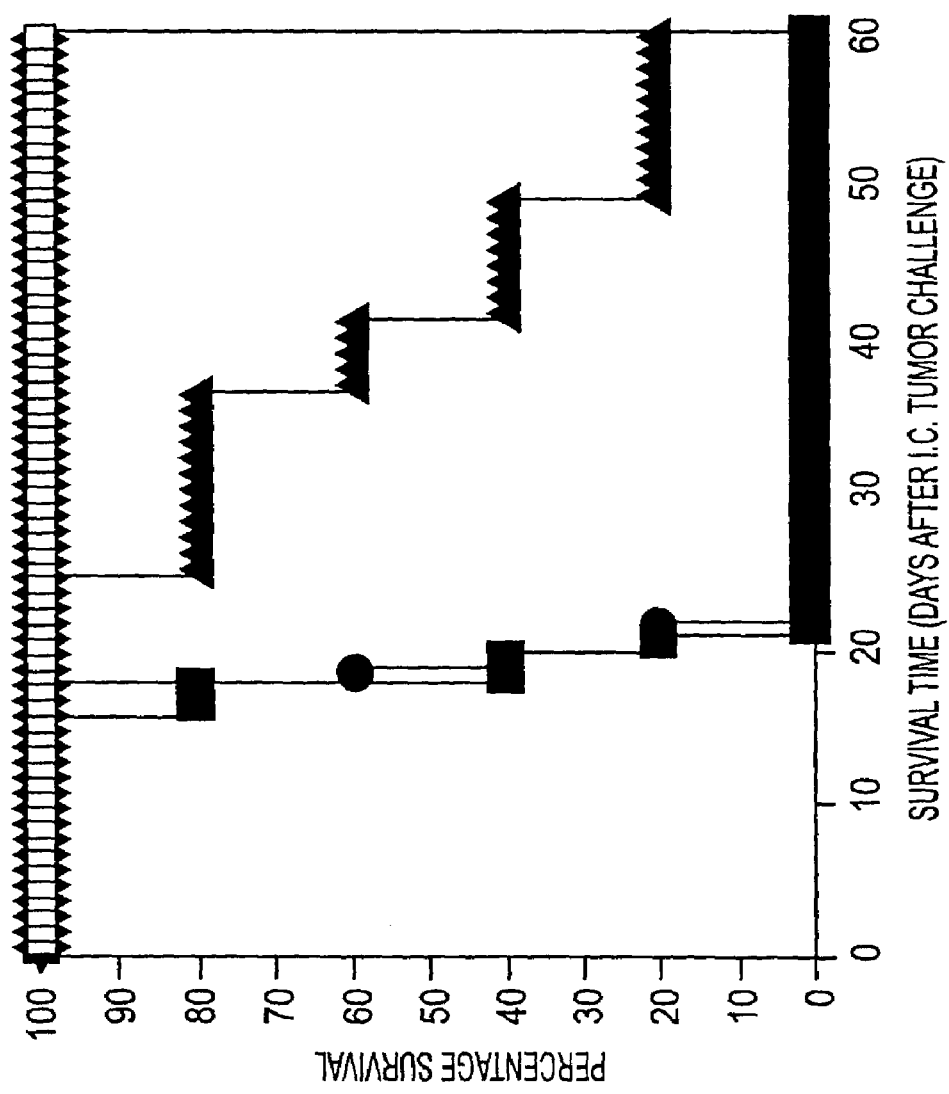
FIG. 7 is a graph plotting percentage survival of CD1 nu/nu mice with intracranial (i.c.) U87 human glioblastoma tumors as a function of survival time, in days after i.c. tumor challenge. Squares represent mice treated with dPBS (n=10); circles represent control mice treated with irrelevant antibody (n=10); and triangles represent mice treated with anti-granulin antibody (n=10).

In this example, nude (nu/nu) mice were challenged with 5×104 U87 cells intracranially, and treated 24 hours later with a single bolus of 10 µl of an anti-human rabbit affinity-purified antibody (10 µg) that specifically recognizes the 55 amino acid sequence corresponding to granulin D, an irrelevant affinity-purified antibody (10 µg), or dPBS injected stereotactically directly into the intracranial tumor. Intratumoral injection of anti-granulin antibody significantly increased median survival by greater than two-fold relative to treatment with dPBS or control antibody. Twenty percent of mice treated with anti-granulin antibody survived longer than 60 days, while all control mice were dead by 21 days (FIG. 7). These results further demonstrate that molecules that interfere with the biological activity of granulin provide an effective therapeutic in the treatment of neural cancer.

From the foregoing it will be appreciated that, although specific embodiments of the invention have been described herein for purposes of illustration, various modifications may be made without deviating from the spirit and scope of the invention. Accordingly, the invention is not limited except as by the appended claims.

REFERENCES

1. Louis, D., and Gusella, J. A tiger behind many doors: multiple genetic pathways to malignant glioma. Trends in Genetics., 11: 412–415, 1995.

2. Varmus, H.: in: Weinberg, R. (ed): Oncogenes and the Molecular Origins of Cancer, Cold Spring Harbor, N.Y.: Cold Spring Harbor Laboratory, 1989, pp 3–44.
3. Furnari, F. et al. Genetics and malignant progression of human brain tumours. Cancer Surv., 25: 233–275, 1995.
4. Cavenee, W. Accumulation of genetic defects during astrocytoma progression. Cancer., 70: 1788–93, 1992.
5. Zhang, L. et al. Gene expression profiles in normal and cancer cells. Science., 276: 1268–72, 1997.
6. Travis, G., and Sutcliff, J. Phenol emulsion-enhanced DNA-driven subtractive cDNA cloning: isolation of low-abundance monkey cortex-specific mRNAs. Proc Nad Acad Sci USA., 85:1696–1700, 1988.
7. Liang, P., and Pardee, A. Differential display of eukaryotic messenger RNA by means of the polymerase chain reaction. Science., 257: 967–971, 1992.
8. Liang, P. et al. Differential display and cloning of messenger RNAs from human breast cancer versus mammary epithelial cells. Cancer Research., 52: 6966–6968, 1992.
9. Linskens, M. et al. Cataloging altered gene expression in young and senescent cells using enhanced differential display. Nucleic Acids Research., 23: 3244–3251, 1995.
10. Uchiyama, C. et al. Differential display of messenger ribonucleic acid: a useful technique for analyzing differential gene expression in human brain tumors. Neurosurgery., 37: 464–469, 1995.
11. Braun, B. et al. Identification of target genes for the Ewing's sarcoma EWS/FL1 fusion protein by representational difference analysis. Mol Cell Biol., 15: 4623–4630, 1995.
12. Hubank, M., and Schatz, D. Identifying differences in mRNA expression by representational difference analysis of cDNA. Nucleic Acids Research., 22: 5640–5648, 1994.
13. Lisitsyn, N. et al. Detection of genetic loss in tumors by representational difference analysis. Cold Spring Harbor Symposia on Quantitative Biology., 59: 585–587, 1994.
14. Lucas, S. et al. Identification of a new MAGE gene with tumor-specific expression by representational difference analysis. Cancer Research., 58: 743–752, 1998.
15. Velculescu, V. et al. Serial analysis of gene expression. Science., 270: 484–487, 1995.
16. Diatchenko, L. et al. Suppression subtractive hybridization: a method for generating differentially regulated or tissue-specific cDNA probes and libraries. Proc. Natl. Acad. Sci. USA., 93: 6025–6030, 1996.
17. Diatchenko, L. et al. Suppression subtractive hybridization: a versatile method for identifying differentially expressed genes. Methods Enzymol., 303: 349–380, 1999.
18. Schena, M. et al. Quantitative monitoring of gene expression patterns with a complementary DNA microarray. Science., 270: 467–470, 1995.
19. Welford, S. et al. Detection of differentially expressed genes in primary tumor tissues using representational differences analysis coupled to microarray hybridization. Nucleic Acids Research., 26: 3059–3065, 1998.
20. DeRisi, J. et al. Exploring the metabolic and genetic control of gene expression on a genomic scale. Science., 278: 680–686, 1997.
21. Iyer, V. et al. The transcriptional program in the response of human fibroblasts to serum. Science., 283: 83–87, 1999.
22. Kornblum, H. et al. Cerebral hemidecortication alters expression of transforming growth factor-a mRNA in the neostriatum of developing rats. Mol Brain Res., 21: 107–114, 1994.
23. Mathern, G. et al. Hippocampal AMPA and NMDA mRNA levels correlate with aberrant fascia dentata mossy fiber sprouting in the pilocarpine model of spontaneous limbic epilepsy. J Neurosci Res., 54: 734–753, 1998.
24. Kumar, S. et al. The hormonal regulation of gene expression of glial markers: glutamine synthetase and glycerol phosphate dehydrogenase in primary cultures of rat brain and in C6 cell line. J Neurosci Res., 16: 251–264, 1986.
25. Estes, M. et al. Characterization of adult human astrocytes derived from explant culture. J Neurosci Res., 27: 697–705, 1990.
26. Bhandari, V. et al. Isolation and sequence of the granulin precursor cDNA from human bone marrow reveals tandem cysteine-rich granulin domains. Proc Natl Acad Sci USA., 89: 1715–1719, 1992.
27. Shoyab, M. et al. Epithelins 1 and 2: Isolation and characterization of two cysteine-rich growth-modulating proteins. Proc Natl Acad Sci USA., 87: 7912–7916, 1990.
28. Bateman, A. et al. Granulins, a novel class of peptide from leukocytes. Biochem Biophys Res Comm., 173: 1161–1168, 1990.
29. Bhandari, V., and Bateman, A. Structure and chromosomal location of the human granulin gene. Biochem-Biophys Res Comm., 188: 57–63, 1992.
30. Zhou, J. et al. Purification of an autocrine growth factor homologous with mouse epithelin from a highly tumorigenic cell line. J Biol Chem., 268: 10863–10869, 1993.
31. Zhang, H., and Serrero, G. Inhibition of tumorigenicity of the teratoma PC cell line by transfection with antisense cDNA for PC cell-derived growth factor (PCDGF, epithelin/granulin precursor). Proc Nad Acad Sci USA., 95: 14202–14207, 1998.
32. Bhandari, V. et al. The complementary deoxyribonucleic acid sequence, tissue distribution, and cellular localization of the rat granulin precursor. Endocrinology., 133: 2683–2689, 1993.
33. Bateman, A., and Bennett, H. Granulins: the structure and function of an emerging family of growth factors. Journal of Endocrinology., 158: 145–151, 1998.
34. Hrabal, R. et al. The hairpin stack fold, a novel protein architecture for a new family of protein growth factors. Nature Structural Biology getters)., 3: 747–752, 1996.
35. Xu, S. et al. The granulin/epithelin precursor abrogates the requirement for the insulin-like growth factor 1 receptor for growth in vitro. J Biol Chem., 273: 20078–20083, 1998.
36. Belcourt, D. et al. Isolation and primary structure of the three major forms of granulin-like peptides from hematopoietic tissues of a teleost fish (*Cyprinus carpio*). J Biol Chem., 268: 9230–9237, 1993.
37. Belcourt, D. et al. Immunocytochemical localization of granulin-1 to mononuclear phagocytic cells of the teleost fish *Cyprinus carpio* and *Carassius auratus*. J Leukoc Biol., 57: 94–100, 1995.
38. Baba, T. et al. Acrogranin, an acrosomal cysteine-rich glycoprotein, is the precursor of the growth-modulating peptides, granulins, and epithelins, and is expressed in somatic as well as male germ cells. Molecular Reproduction and Development., 34: 233–243, 1993.
39. Baba, T. et al. Exon/intron organization of the gene encoding the mouse epithelin/granulin precursos (acrogranin). FEBS., 322: 89–94, 1993.
40. Trinh, D. et al. Epithelin/granulin growth factors: extracellular cofactors for HIV-1 and HIV-2 Tat proteins. Biochem Biophys Res Commun., 256: 299–306, 1999.

41. Boguski, M., and Schuler, G. ESTablishing a human transcript map. Nature Genetics., 10: 369–371, 1995.
42. Bhandari, V. et al. Structural and functional analysis of a promoter of the human granulin/epithelin gene. Biochem J., 319: 441–447, 1996.
43. Nagane, M. et al. Advances in the molecular genetics of gliomas. Current Opinion Oncology., 9: 215–222, 1997.
44. Culouscou, J.-M. et al. Biochemical analysis of the epithelin receptor. Journal of Biol Chem., 268: 10458–10462, 1993.
45. Maguire, H. J., and Greene, M. The neu (c-erbB-2) oncogene. Seminars Oncol., 16: 148–155, 1989.
46. Kasai, H. et al. Detection of chromosomal numerical aberration in glioma by FISH. Human Cell., 6: 62–65, 1993.
47. Arnoldus, E. et al. Interphase cytogenetics: a new tool for the study of genetic changes in brain tumors. j Neurosurg., 76: 997–1003, 1992.
48. Dietzmann, K., and von Bossanyi, P. Coexpression of epidermal growth factor receptor protein and c-erbB-2 oncoprotein in human astrocytic tumors. An immunohistochemical study. Zentralbl Pathol., 140: 335–341, 1994.
49. Engelhard, H. et al. Analysis of c-erbB2 protein content in human glioma cells and tumor tissue. J Neurooncol., 23: 31–40, 1995.
50. von Bossanyi, P. et al. Correlation of TGF-a and EGF-receptor expression with proliferative activity in human astrocytic gliomas. Pathol Res Pract., 194: 141–147, 1998.

What is claimed is:

1. A method for detecting cancer in a neural tissue comprising contacting a specimen containing the tissue with a molecule that specifically recognizes and binds a granulin D or a polynucleotide that encodes granulin D, wherein the molecule is an antibody or a polynucleotide, and detecting binding of the molecule to granulin D or a polynucleotide that encodes granulin D, whereby the binding is indicative of cancer.

2. The method of claim 1, wherein the molecule is an antibody directed against a granulin D peptide.

3. The method of claim 1, wherein the molecule is an antisense nucleotide directed against a granulin D nucleic acid molecule.

4. The method of claim 1, wherein the tissue is human.

5. The method of claim 1, wherein the tissue comprises a tumor specimen.

6. The method of claim 1, wherein the specimen comprises cerebrospinal fluid.

7. The method of claim 1, wherein the neural cancer is a glioblastoma, astrocytoma, or oligodendroglioma.

8. The method of claim 1, wherein the molecule is an oligonucleotide primer directed against a granulin D nucleic acid molecule.

9. The method of claim 1, wherein the molecule is an oligonucleotide probe directed against a granulin D nucleic acid molecule.

10. The method of claim 1, wherein the molecule is labeled with a detectable marker.

11. The method of claim 10, further comprising detecting the presence of the detectable marker, whereby the presence of the detectable marker is indicative of the presence of cancer.

* * * * *